US008569219B2

(12) United States Patent
Koivisto et al.

(10) Patent No.: US 8,569,219 B2
(45) Date of Patent: *Oct. 29, 2013

(54) HIGH ALCOHOL CONTENT FOAMING COMPOSITIONS COMPRISING AN ANIONIC PHOSPHATE FLUOROSURFACTANT

(75) Inventors: Bruce Michael Koivisto, Willsonville (CA); Maria Teresa Fernandez de Castro, Brantford (CA)

(73) Assignee: Deb Worldwide Healthcare Inc., Brantford, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/479,630

(22) Filed: May 24, 2012

(65) Prior Publication Data

US 2012/0232161 A1    Sep. 13, 2012

Related U.S. Application Data

(60) Continuation of application No. 12/659,063, filed on Feb. 24, 2010, now abandoned, which is a division of application No. 11/507,626, filed on Aug. 22, 2006, now Pat. No. 7,683,018, which is a continuation of application No. 10/952,474, filed on Sep. 29, 2004, now Pat. No. 7,199,090.

(60) Provisional application No. 60/591,601, filed on Jul. 28, 2004, provisional application No. 60/506,172, filed on Sep. 29, 2003.

(51) Int. Cl.
*C11D 3/43* (2006.01)
*C11D 3/24* (2006.01)

(52) U.S. Cl.
USPC ........... 510/138; 510/130; 510/149; 510/157; 510/432; 510/436

(58) Field of Classification Search
USPC .................. 510/130, 138, 149, 157, 432, 436
See application file for complete search history.

(56) References Cited

U.S. PATENT DOCUMENTS

| | | |
|---|---|---|
| 2,054,989 A | 9/1936 | Moore |
| 2,559,749 A | 7/1951 | Benning |
| 2,597,702 A | 5/1952 | Benning |
| 2,599,140 A | 6/1952 | Taub |
| 2,855,367 A | 10/1958 | Buck |
| 3,131,152 A | 4/1964 | Klausner |
| 3,131,153 A | 4/1964 | Klausner |
| 3,395,214 A | 7/1968 | Mummert |
| 3,708,435 A | 1/1973 | Starkman |
| 3,709,437 A | 1/1973 | Wright |
| 3,770,648 A | 11/1973 | Mackles |
| 3,787,566 A | 1/1974 | Gauvreau et al. |
| 3,824,303 A | 7/1974 | Lanzet |
| 3,928,558 A | 12/1975 | Cheesman et al. |
| 3,962,150 A | 6/1976 | Viola |
| 3,963,507 A | 6/1976 | Kuramoto et al. |
| 4,018,364 A | 4/1977 | Wright |
| 4,086,178 A | 4/1978 | Walker |
| 4,220,665 A | 9/1980 | Klein |
| 4,225,456 A | 9/1980 | Schmidt et al. |
| 4,311,695 A | 1/1982 | Starch |
| 4,313,978 A | 2/1982 | Stevens |
| 4,336,151 A | 6/1982 | Like et al. |
| 4,440,652 A | 4/1984 | Hunter |
| 4,440,653 A * | 4/1984 | Briscoe et al. ................ 507/202 |
| 4,454,060 A | 6/1984 | Lai et al. |
| 4,478,853 A | 10/1984 | Chaussee |
| 4,511,486 A | 4/1985 | Shah |
| 4,559,226 A | 12/1985 | Fogel et al. |
| 4,567,038 A | 1/1986 | Ciaudelli et al. |
| 4,584,189 A | 4/1986 | Leipold |
| 4,613,592 A | 9/1986 | Benzoni |
| 4,714,568 A | 12/1987 | Hurnik et al. |
| 4,772,592 A | 9/1988 | Benzoni |
| 4,826,828 A | 5/1989 | Wilmott et al. |
| 4,839,166 A | 6/1989 | Grollier et al. |
| 4,839,167 A | 6/1989 | Yamamoto et al. |

(Continued)

FOREIGN PATENT DOCUMENTS

AU    2003203452 B1    10/2004
CA      2 323 780 A1     4/2001

(Continued)

OTHER PUBLICATIONS

U.S. Appl. No. 12/514,326, filed May 11, 2009 and entitled "Compositions, in Particular Cream to Protect Against Cold".
Notice of Allowance and Fee(s) Due and Notice of Allowability mailed Nov. 24, 2009 for U.S. Appl. No. 11/151,563, filed Jun. 13, 2005.
Interview Summary with Notification Date of Nov. 24, 2009 for U.S. Appl. No. 11/312,559, filed Dec. 21, 2005.
Office Action for Canadian Patent Application No. 2,540,085 dated Oct. 29, 2008.
Examiner's first report on Australian Patent Application No. 2004 275900 dated May 21, 2009.
Office Action mailed Dec. 4, 2008 in U.S. Appl. No. 11/312,559.

(Continued)

*Primary Examiner* — Charles Boyer
(74) *Attorney, Agent, or Firm* — Neal, Gerber & Eisenberg LLP

(57) ABSTRACT

A "high lower alcohol content" (>40% v/v of a $C_{1-4}$ alcohol) liquid composition is able to be dispensed as a stable foam with the use of non-propellant foam dispensing devices from non-pressurized containers. The liquid compositions comprise an alcohol, $C_{1-4}$ (>40% v/v), a fluorosurfactant of at least 0.001% by weight to prepare a foamable composition, 0-10% w/w of additional minor components added to obtain the desired performance (a foamable composition with a viscosity less than 4,000 cps), and the balance being purified water. The compositions may include emulsifier-emollients and moisturizers, secondary surfactants, foam stabilizers, fragrances, antimicrobial agents, other type of medicinal ingredients, and the like ingredients or additives or combinations thereof commonly added to alcohol gels or foams, aerosol compositions or to toiletries, cosmetics, pharmaceuticals and the like.

37 Claims, No Drawings

(56) References Cited

U.S. PATENT DOCUMENTS

| | | |
|---|---|---|
| 4,857,302 A | 8/1989 | Decker et al. |
| 4,897,262 A | 1/1990 | Nandagiri et al. |
| 4,906,459 A | 3/1990 | Cobb et al. |
| 4,915,934 A | 4/1990 | Tomlinson |
| 4,919,837 A | 4/1990 | Glack |
| 4,956,170 A | 9/1990 | Lee |
| 4,956,173 A | 9/1990 | Le Fur et al. |
| 4,981,678 A | 1/1991 | Tomlinson |
| 4,983,377 A | 1/1991 | Murphy et al. |
| 4,986,922 A | 1/1991 | Snow et al. |
| 4,988,453 A | 1/1991 | Chambers |
| 5,015,228 A | 5/1991 | Columbus et al. |
| 5,043,088 A | 8/1991 | Falla |
| 5,047,249 A | 9/1991 | Rothman et al. |
| 5,073,371 A | 12/1991 | Turner et al. |
| 5,100,658 A | 3/1992 | Bolich, Jr. et al. |
| 5,104,646 A | 4/1992 | Bolich, Jr. et al. |
| 5,122,541 A | 6/1992 | Eggensperger et al. |
| 5,128,123 A | 7/1992 | Brewster et al. |
| 5,167,950 A | 12/1992 | Lina |
| 5,180,584 A | 1/1993 | Sebag et al. |
| 5,204,099 A | 4/1993 | Barbier et al. |
| D338,585 S | 8/1993 | Bell |
| 5,232,691 A | 8/1993 | Lemole |
| 5,256,401 A | 10/1993 | Duckenfield |
| 5,265,772 A | 11/1993 | Bartasevich |
| 5,266,598 A | 11/1993 | Ninomiya et al. |
| D343,751 S | 2/1994 | Bell |
| 5,288,486 A | 2/1994 | White |
| 5,290,555 A | 3/1994 | Guthauser et al. |
| D346,332 S | 4/1994 | Kanfer |
| 5,300,284 A | 4/1994 | Wiechers et al. |
| 5,314,684 A | 5/1994 | Horoschak et al. |
| 5,336,497 A | 8/1994 | Guerrero et al. |
| 5,352,437 A | 10/1994 | Nakagawa et al. |
| 5,362,484 A | 11/1994 | Wood et al. |
| 5,370,267 A | 12/1994 | Schroeder |
| 5,415,811 A | 5/1995 | Wile |
| 5,441,178 A | 8/1995 | Wysocki |
| 5,443,236 A | 8/1995 | Bell |
| 5,445,288 A | 8/1995 | Banks |
| 5,449,137 A | 9/1995 | Bell |
| 5,462,688 A | 10/1995 | Lippman |
| D365,509 S | 12/1995 | Bell |
| D365,518 S | 12/1995 | Wysocki |
| D365,755 S | 1/1996 | Kanfer |
| 5,484,597 A | 1/1996 | Slavtcheff et al. |
| 5,494,533 A | 2/1996 | Woodin, Jr. et al. |
| 5,523,014 A | 6/1996 | Dolan |
| 5,547,662 A | 8/1996 | Khan et al. |
| 5,549,888 A | 8/1996 | Venkateswaran |
| 5,558,453 A | 9/1996 | Bell |
| 5,567,428 A | 10/1996 | Hughes |
| 5,587,358 A | 12/1996 | Sukigara |
| 5,607,980 A | 3/1997 | McAtee et al. |
| 5,612,324 A | 3/1997 | Guang Lin et al. |
| 5,625,659 A | 4/1997 | Sears |
| 5,626,853 A | 5/1997 | Bara et al. |
| 5,629,006 A | 5/1997 | Hoang |
| 5,635,462 A | 6/1997 | Fendler |
| 5,635,469 A | 6/1997 | Fowler et al. |
| D383,001 S | 9/1997 | Bell |
| 5,662,893 A | 9/1997 | George et al. |
| 5,665,332 A | 9/1997 | Mundschenk et al. |
| D385,795 S | 11/1997 | Wysocki |
| 5,690,921 A | 11/1997 | Lang et al. |
| 5,693,255 A | 12/1997 | Okamoto et al. |
| 5,718,353 A | 2/1998 | Kanfer |
| 5,719,113 A | 2/1998 | Fendler |
| D392,136 S | 3/1998 | Ross |
| 5,733,535 A | 3/1998 | Hollingshead et al. |
| 5,756,077 A | 5/1998 | Syed et al. |
| 5,767,054 A | 6/1998 | Sprugel et al. |
| 5,767,161 A | 6/1998 | Stroppolo et al. |
| 5,776,430 A | 7/1998 | Osborne et al. |
| 5,789,371 A | 8/1998 | Tracy et al. |
| 5,824,320 A | 10/1998 | Rouillard et al. |
| D400,799 S | 11/1998 | Bell |
| 5,834,516 A | 11/1998 | O'Lenick, Jr. |
| 5,856,347 A | 1/1999 | Hashiguchi et al. |
| 5,863,884 A | 1/1999 | Lafreniere |
| 5,902,778 A | 5/1999 | Hartmann et al. |
| 5,906,808 A | 5/1999 | Osborne |
| D411,456 S | 6/1999 | Mast |
| 5,908,619 A | 6/1999 | Scholz |
| 5,919,439 A | 7/1999 | Torgerson et al. |
| 5,922,663 A | 7/1999 | Gabriel et al. |
| 5,928,993 A | 7/1999 | Johansson |
| 5,935,587 A | 8/1999 | Cauwet et al. |
| 5,944,227 A | 8/1999 | Schroeder |
| 5,951,993 A | 9/1999 | Scholz et al. |
| 5,952,290 A | 9/1999 | Li et al. |
| 5,955,408 A | 9/1999 | Kaiser |
| 5,955,416 A | 9/1999 | Baillely et al. |
| D415,343 S | 10/1999 | Maddox |
| 5,972,356 A | 10/1999 | Peffly et al. |
| D416,417 S | 11/1999 | Ross |
| 5,980,876 A | 11/1999 | Peffy |
| 5,996,851 A | 12/1999 | Dolan |
| D418,708 S | 1/2000 | Kanfer |
| 6,019,997 A | 2/2000 | Scholz et al. |
| 6,022,551 A | 2/2000 | Jampani et al. |
| 6,039,965 A | 3/2000 | Donian et al. |
| D422,828 S | 4/2000 | Kanfer |
| 6,065,639 A | 5/2000 | Maddox |
| 6,086,856 A | 7/2000 | Saferstein et al. |
| 6,090,395 A | 7/2000 | Asmus |
| 6,117,440 A * | 9/2000 | Suh et al. .................. 424/407 |
| 6,130,253 A | 10/2000 | Franklin et al. |
| 6,183,766 B1 | 2/2001 | Sine et al. |
| 6,217,885 B1 | 4/2001 | Röder et al. |
| 6,255,265 B1 | 7/2001 | Van Gunst |
| 6,262,128 B1 | 7/2001 | Stern et al. |
| 6,264,929 B1 | 7/2001 | Karlen et al. |
| 6,265,363 B1 | 7/2001 | Viscovitz |
| 6,267,976 B1 | 7/2001 | Barnhart |
| 6,274,124 B1 | 8/2001 | Vollhardt |
| 6,277,359 B1 | 8/2001 | Raths et al. |
| 6,319,489 B1 | 11/2001 | Ashton et al. |
| 6,319,958 B1 | 11/2001 | Johnson et al. |
| 6,333,039 B1 | 12/2001 | Fendler et al. |
| 6,339,165 B1 | 1/2002 | Endo et al. |
| 6,342,470 B1 | 1/2002 | Aronson |
| 6,352,701 B1 | 3/2002 | Scholz et al. |
| 6,358,914 B1 | 3/2002 | Gabriel et al. |
| 6,376,438 B1 | 4/2002 | Rosenberger et al. |
| 6,383,505 B1 | 5/2002 | Kaiser |
| 6,383,997 B1 | 5/2002 | McManus |
| 6,410,005 B1 | 6/2002 | Galleguillos et al. |
| 6,423,329 B1 * | 7/2002 | Sine et al. .................. 424/405 |
| 6,462,002 B2 | 10/2002 | Saxena |
| 6,471,983 B1 | 10/2002 | Veeger et al. |
| 6,472,356 B2 | 10/2002 | Narula et al. |
| 6,479,442 B1 | 11/2002 | Berube |
| 6,489,275 B1 | 12/2002 | Veeger et al. |
| 6,491,840 B1 | 12/2002 | Frankenbach et al. |
| 6,497,864 B1 | 12/2002 | Samain et al. |
| 6,518,228 B1 | 2/2003 | Jorgensen |
| 6,524,494 B2 | 2/2003 | Hart et al. |
| 6,524,594 B1 | 2/2003 | Santora |
| 6,528,544 B2 | 3/2003 | Stern et al. |
| 6,534,069 B1 | 3/2003 | Asmus et al. |
| 6,537,952 B2 | 3/2003 | Hayward |
| 6,551,605 B2 | 4/2003 | Bondo |
| 6,555,508 B1 | 4/2003 | Paul |
| 6,562,360 B2 | 5/2003 | Scholz et al. |
| 6,582,711 B1 | 6/2003 | Asmus et al. |
| 6,592,880 B1 | 7/2003 | Jager |
| 6,610,315 B2 | 8/2003 | Scholz et al. |
| 6,617,294 B2 | 9/2003 | Narula et al. |
| 6,623,744 B2 | 9/2003 | Asmus |
| 6,638,527 B2 | 10/2003 | Gott |
| 6,641,825 B2 | 11/2003 | Scholz |
| 6,664,256 B1 | 12/2003 | Oohkuchi et al. |

(56) References Cited

U.S. PATENT DOCUMENTS

| | | |
|---|---|---|
| 6,664,356 B1 | 12/2003 | Shih |
| 6,666,217 B2 | 12/2003 | Elsner |
| 6,685,952 B1 | 2/2004 | Ma et al. |
| 6,689,593 B2 | 2/2004 | Millis |
| 6,696,053 B1 | 2/2004 | Ma et al. |
| 6,696,397 B2 | 2/2004 | Staats |
| 6,703,007 B2 | 3/2004 | Glenn, Jr. |
| 6,706,675 B1 | 3/2004 | Demson |
| 6,709,647 B2 | 3/2004 | Bhakoo |
| 6,710,022 B1 | 3/2004 | Kwetkat et al. |
| 6,723,689 B1 | 4/2004 | Hoang |
| 6,730,621 B2 | 5/2004 | Gott |
| 6,759,376 B2 | 7/2004 | Zhang |
| 6,762,158 B2 | 7/2004 | Lukenbach |
| 6,777,384 B2 | 8/2004 | Raths et al. |
| 6,780,826 B2 | 8/2004 | Zhang |
| 6,794,345 B2 | 9/2004 | Elsner et al. |
| 6,797,687 B2 | 9/2004 | Kischkel et al. |
| 6,805,141 B2 | 10/2004 | Elsner et al. |
| 6,815,410 B2 | 11/2004 | Boutique |
| 6,818,603 B2 | 11/2004 | Aleles |
| 6,846,846 B2 | 1/2005 | Modak et al. |
| 6,875,539 B2 | 4/2005 | Ophardt |
| 6,884,763 B2 | 4/2005 | Willard |
| 6,946,120 B2 | 9/2005 | Wai-Chiu et al. |
| 6,977,082 B2 | 12/2005 | Seitz, Jr. et al. |
| 7,081,246 B2 | 7/2006 | Asmus et al. |
| 7,141,237 B2 | 11/2006 | Abram et al. |
| 7,163,916 B2 | 1/2007 | Alief et al. |
| 7,164,041 B1 | 1/2007 | Moore et al. |
| 7,166,435 B2 | 1/2007 | Rosenbloom |
| 7,199,090 B2 | 4/2007 | Koivisto |
| 7,241,452 B2 | 7/2007 | Veeger et al. |
| 7,297,675 B2 | 11/2007 | Alief et al. |
| 7,393,817 B2 | 7/2008 | Kwetket et al. |
| 7,530,477 B2 | 5/2009 | Ophardt |
| 7,547,732 B2 | 6/2009 | Moore et al. |
| 7,566,460 B2 | 7/2009 | Asmus et al. |
| 7,597,898 B2 | 10/2009 | Birkel et al. |
| 7,651,990 B2 | 1/2010 | Asmus |
| 7,670,615 B2 | 3/2010 | Veeger |
| 7,683,018 B2 | 3/2010 | Koivisto et al. |
| 7,723,279 B2 | 5/2010 | Lestage et al. |
| 7,790,663 B2 | 9/2010 | Lestage et al. |
| 7,803,390 B2 | 9/2010 | Asmus et al. |
| 7,842,725 B2 | 11/2010 | Wegner et al. |
| 7,850,048 B2 | 12/2010 | Arminak |
| 8,058,315 B2 | 11/2011 | Wegner et al. |
| 2002/0022660 A1 | 2/2002 | Jampani |
| 2002/0028187 A1 | 3/2002 | Nekludoff et al. |
| 2002/0039562 A1 | 4/2002 | Kobayashi et al. |
| 2002/0098159 A1* | 7/2002 | Wei et al. ............ 424/70.1 |
| 2002/0106399 A1 | 8/2002 | Durden |
| 2002/0108640 A1 | 8/2002 | Barger et al. |
| 2002/0127253 A1 | 9/2002 | Scholz et al. |
| 2002/0142018 A1 | 10/2002 | Scholz et al. |
| 2002/0151446 A1 | 10/2002 | Piterski et al. |
| 2002/0160029 A1 | 10/2002 | Asmus et al. |
| 2002/0160924 A1 | 10/2002 | Bertrem et al. |
| 2002/0177535 A1 | 11/2002 | Piterski et al. |
| 2002/0187908 A1 | 12/2002 | Gagilardi et al. |
| 2003/0134761 A1 | 7/2003 | Sebillotte-Arnaud et al. |
| 2003/0203824 A1 | 10/2003 | Staats |
| 2003/0211066 A1 | 11/2003 | Scholz et al. |
| 2003/0213542 A1 | 11/2003 | Kobayashi et al. |
| 2003/0215418 A1 | 11/2003 | Asmus et al. |
| 2003/0235550 A1 | 12/2003 | Pan et al. |
| 2004/0001797 A1 | 1/2004 | Saud et al. |
| 2004/0071748 A1 | 4/2004 | Asmus et al. |
| 2004/0072700 A1 | 4/2004 | Gupta |
| 2004/0102429 A1 | 5/2004 | Modak et al. |
| 2004/0170592 A1 | 9/2004 | Veeger et al. |
| 2004/0191195 A1 | 9/2004 | Collins et al. |
| 2004/0191274 A1 | 9/2004 | Grayson et al. |
| 2004/0219227 A1 | 11/2004 | Modak et al. |
| 2004/0241099 A1 | 12/2004 | Popp et al. |
| 2004/0247685 A1 | 12/2004 | Modak et al. |
| 2004/0265240 A1 | 12/2004 | Tamarkin et al. |
| 2005/0003990 A1 | 1/2005 | Smith et al. |
| 2005/0031580 A1 | 2/2005 | Allef et al. |
| 2005/0031653 A1 | 2/2005 | Kwetkat et al. |
| 2005/0063925 A1 | 3/2005 | Candau et al. |
| 2005/0109981 A1 | 5/2005 | Tucker et al. |
| 2005/0129626 A1 | 6/2005 | Koivisto et al. |
| 2005/0152931 A1 | 7/2005 | SaNoguiera et al. |
| 2005/0222001 A1 | 10/2005 | Baumeister et al. |
| 2005/0226838 A1 | 10/2005 | Krause et al. |
| 2005/0277574 A1 | 12/2005 | Niedbala et al. |
| 2006/0018847 A1 | 1/2006 | Kroepke et al. |
| 2006/0104911 A1 | 5/2006 | Novak |
| 2006/0104919 A1 | 5/2006 | Novak |
| 2006/0110416 A1 | 5/2006 | Ryles et al. |
| 2006/0165627 A1 | 7/2006 | Allef et al. |
| 2006/0182690 A1 | 8/2006 | Veeger et al. |
| 2006/0198859 A1 | 9/2006 | Allef et al. |
| 2006/0204468 A1 | 9/2006 | Allef et al. |
| 2006/0257334 A1 | 11/2006 | Dahms et al. |
| 2006/0263396 A1 | 11/2006 | Asmus et al. |
| 2006/0275226 A1 | 12/2006 | Dahms et al. |
| 2006/0281663 A1 | 12/2006 | Asmus et al. |
| 2007/0027055 A1 | 2/2007 | Koivisto et al. |
| 2007/0041927 A1 | 2/2007 | Blaeser et al. |
| 2007/0065383 A1 | 3/2007 | Fernandez de Castro et al. |
| 2007/0092470 A1 | 4/2007 | Allef et al. |
| 2007/0141007 A1 | 6/2007 | Glynn et al. |
| 2007/0148101 A1 | 6/2007 | Snyder et al. |
| 2007/0179207 A1 | 8/2007 | Fernandez de Castro et al. |
| 2007/0258911 A1 | 11/2007 | Fernandez de Castro et al. |
| 2008/0051312 A1 | 2/2008 | Lestage et al. |
| 2008/0108704 A1 | 5/2008 | Asmus et al. |
| 2008/0145320 A1 | 6/2008 | Wenk et al. |
| 2008/0178899 A1 | 7/2008 | Moenks et al. |
| 2008/0207767 A1 | 8/2008 | Dobos |
| 2008/0293825 A1 | 11/2008 | Littau et al. |
| 2008/0305056 A1 | 12/2008 | Jenni et al. |
| 2009/0054521 A1 | 2/2009 | Henwerth et al. |
| 2009/0098067 A1 | 4/2009 | Seidling et al. |
| 2009/0326076 A1 | 12/2009 | Asmus |
| 2010/0022660 A1 | 1/2010 | Wegner et al. |
| 2010/0069505 A1 | 3/2010 | Veeger et al. |
| 2010/0160415 A1 | 6/2010 | Koivisto et al. |
| 2010/0187263 A1 | 7/2010 | Lestage et al. |
| 2010/0234475 A1 | 9/2010 | Wegner et al. |
| 2010/0327013 A1 | 12/2010 | Asmus |
| 2010/0331411 A1 | 12/2010 | Asmus |
| 2011/0104079 A1 | 5/2011 | Snyder et al. |
| 2011/0110869 A1 | 5/2011 | Scholtz et al. |
| 2011/0201693 A1 | 8/2011 | Littau |
| 2011/0319364 A1 | 12/2011 | Wegner et al. |

FOREIGN PATENT DOCUMENTS

| | | |
|---|---|---|
| CA | 2587086 | 4/2006 |
| DE | 2852583 | 6/1979 |
| DE | 3306593 A1 | 2/1983 |
| DE | 3306593 | 9/1983 |
| DE | 19523320 | 1/1997 |
| DE | 69512841 T2 | 5/2000 |
| DE | 69630221 | 7/2004 |
| DE | 10 2004 050 211 A1 | 4/2006 |
| EP | 0160051 | 11/1985 |
| EP | 0213527 | 3/1987 |
| EP | 0117889 | 11/1987 |
| EP | 0260641 | 3/1988 |
| EP | 0384126 | 8/1990 |
| EP | 0689767 | 1/1996 |
| EP | 0882446 | 12/1998 |
| EP | 0990412 | 4/2000 |
| EP | 1 118 655 | 7/2001 |
| EP | 1 584 323 | 10/2005 |
| EP | 1 893 167 A1 | 3/2008 |
| EP | 1811013 B1 | 8/2009 |
| GB | 2010874 | 7/1979 |
| JP | 11349418 | 12/1999 |

(56) References Cited

FOREIGN PATENT DOCUMENTS

| | | |
|---|---|---|
| JP | 2006279268 | 10/2006 |
| JP | 2007285808 | 11/2007 |
| WO | 93/00089 | 1/1993 |
| WO | 93/03704 | 3/1993 |
| WO | 93/07250 | 4/1993 |
| WO | 95/01384 | 1/1995 |
| WO | 95/03772 | 2/1995 |
| WO | 97/00667 | 1/1997 |
| WO | 97/00667 A1 | 1/1997 |
| WO | 97/00668 | 1/1997 |
| WO | 99/20250 | 4/1999 |
| WO | 00/06107 | 2/2000 |
| WO | 00/47183 | 8/2000 |
| WO | 02062936 A1 | 8/2002 |
| WO | 03/028671 | 4/2003 |
| WO | 03/034994 | 5/2003 |
| WO | 03/053388 | 7/2003 |
| WO | 04000016 A2 | 12/2003 |
| WO | 2005/030917 | 9/2004 |
| WO | 2005-051341 | 6/2005 |
| WO | 2005/123012 | 12/2005 |
| WO | 2006/042588 | 4/2006 |
| WO | 2006/066888 | 6/2006 |
| WO | WO 2006/094387 | 9/2006 |
| WO | 2006138111 | 12/2006 |
| WO | 2007095008 | 8/2007 |
| WO | 2008/132621 A1 | 11/2008 |
| WO | 2010/010475 | 1/2010 |

OTHER PUBLICATIONS

Office Action mailed Feb. 13, 2009 in U.S. Appl. No. 11/312,559.
Office Action mailed Mar. 16, 2009 in U.S. Appl. No. 11/312,559.
Office Action mailed Oct. 21, 2008 in U.S. Appl. No. 11/151,563.
Office Action mailed Jul. 14, 2009 in U.S. Appl. No. 11/312,559.
Notice of Allowance mailed Jun. 2, 2009 in U.S. Appl. No. 11/151,563.
Interview Summary dated Jul. 14, 2009 for U.S. Appl. No. 11/312,559, filed Dec. 21, 2005.
European Patent Specification EP 1 811 01381 published Aug. 12, 2009.
Request for Foreign Priority mailed Aug. 19, 2009 for U.S. Appl. No. 11/312,559, filed Dec. 21, 2005.
Request for RCE dated Sep. 1, 2009 in U.S. Appl. No. 11/151,563, filed Jun. 13, 2005.
Notice of Allowability dated Sep. 21, 2009 in U.S. Appl. No. 11/151,563, filed Jun. 13, 2005.
Non-Final Rejection mailed Sep. 17, 2009 for U.S. Appl. No. 12/032,083, filed Feb. 15, 2008.
Response dated Oct. 12, 2009 to European Patent Application No. 08250626.2.
Canadian Examination Report dated Oct. 13, 2009 in Application Serial No. 2,595,025.
Notice of Allowability mailed Oct. 13, 2009 in U.S. Appl. No. 11/312,559, filed Dec. 21, 2005.
Office Action dated Oct. 15, 2009 in U.S. Appl. No. 11/438,664, filed May 22, 2006.
Examination Report dated Jul. 20, 2009 for New Zealand Patent Application No. 561741.
Defendant BETCO, Corporation's Initial Disclosures Pursuant to Fed. R. Civ. p. 26(a) (1), *DEB Worldwide Healthcare, Inc.* v. *BETCO, Corp.*, Case No. 3:08-cv-00052-bbc, US District Court for the Western District of Wisconsin, Apr. 2, 2008.
First Amended Complaint, *DEB Worldwide Healthcare, Inc.* v. *BETCO, Corp.*, Case No. 3:08-cv-00052-bbc, US District Court for the Western District of Wisconsin, document #21, Apr. 21, 2008.
Complaint, *DEB Worldwide Healthcare, Inc.* v. *BETCO, Corp.*, Case No. 3:08-cv-00052-bbc, US District Court for the Western District of Wisconsin, document #1, Jan. 22, 2008.
Dewar et al., Effectiveness of Septisol Antiseptic Foam as a Surgical Scrub Agent, Applied Microbiology, Oct. 1973, vol. 26, No. 4, p. 544-549.

Beck, W, Alcohol foam for hand disinfection, AORN Journal, Dec. 1980, vol. 32, No. 6, p. 1087-1088.
3M Fluorad Well Stimulation Additive FC-742 Foamer for Aqueous/Alcoholic Fluids, 3M 1987,6 pages.
Sandra J. Pfaff, Letters to the Editor, Alcohol Foam Use Questioned, AORN Journal, Dec. 1989, vol. 50, No. 6, 1 page.
3M Product Information Well Stimulation Additive FC-742, Foamer for Aqueous/Alcoholic Fluids, 1994,4 pages.
Zonyl FSP fluorosurfactant, Technical Information, DuPont, 1998,2 pages.
Rosen et al., Industrial Utilization of Surfactants; Principles and Practice, AOCS Press, 2000, 4 pages.
Pabon et al., Fluorinated surfactants: synthesis, properties effluent treatment, J. Fluorine Chem. 114 (2002), p. 149-156.
Degussa, Creating Essentials, "Goldschmidt Personal Care," Catalog of Products, May 2003.
Product Information Sheet, Mackanate DC-50, Mcintyre Group Ltd., 1 page.
Product Information Sheet, Dow Corning 2501, Cosmetic Wax, 4 sheets.
Product Description, GE Silicones, SF1202, Dec. 22, 2004,6 sheets.
Product Description, GE Silicones, SF1388, Dec. 22, 2004, 2 sheets.
Product Information, DOW Corning, Sylgard 309 Silicone Surfactant, 3 sheets.
Product Description, GE Advance Materials Silicones, SF1388, Jan. 5, 2005,2 sheets.
Office Action dated Mar. 28, 2012 in U.S. Appl. No. 13/095,698.
Amendment dated Jun. 28, 2012 in U.S. Appl. No. 13/095,696.
US 7,754,762, Jul. 2010, Wegner et al. (withdrawn).
U.S. Office Action mailed Jun. 28, 2010 for U.S. Appl. No. 11/438,664.
Preliminary Amendment dated Jul. 24, 2008 in U.S. Appl. No. 12/179,410 (Publication No. 2008-0293825 published on Nov. 27, 2008).
International Search Report for International Application No. PCT/US2006/021904 mailed Oct. 24, 2006.
Notice of Allowance dated Jul. 20, 2010 for U.S. Appl. No. 12/179,382.
Supplemental Response and Amendment filed on Aug. 13, 2010 for U.S. Appl. No. 12/032,083.
Request for Continued Examination filed on Jul. 6, 2010 for U.S. Appl. No. 12/032,083.
Advisory Action Communication mailed Jun. 29, 2010 for U.S. Appl. No. 12/032,083.
U.S. Office Action mailed Aug. 3, 2010 for U.S. Appl. No. 11/075,287.
U.S. Office Action mailed Aug. 3, 2010 for U.S. Appl. No. 11/369,381.
Response and Amendment after Final Office Action filed on Jun. 2, 2010 for U.S. Appl. No. 12/032,083.
Communication of Notices of Opposition to a European Patent (EP 1 811 013) filed by Ecolab, Inc., 3M Innovative Properties Company and DEB Worldwide Healthcare Inc. against Gojo Industries dated Jun. 16, 2010.
Affidavit of Bruce Michael Koivisto signed and dated on May 17, 2010.
"Dow Corning® 190 Fluid" product information. Dow Corning, Midland, MI Feb. 24, 2010, Ref. No. 22-1616E-01 (3 pages).
Printout of http://www.rexamairspray.com/products-foampump.php Oct. 5, 2010 (2 pages).
Notice of Opposition to a European Patent (EP 1 811 013) filed by 3M Innovative Properties Company against Gojo Industries dated May 12, 2010.
Notice of Opposition to a European Patent (EP 1 811 013) filed by Ecolab, Inc. against Gojo Industries dated May 6, 2010.
Affidavit of Caroline Fellows dated May 10, 2010.
Technical Information for LUVIQUAT® PQ 11, BASF, May 1997 (3 pages).
Response and Amendment dated Apr. 7, 2010 for U.S. Appl. No. 11/438,664.
Declaration of Amanda J. Copeland dated Apr. 7, 2010.

(56) References Cited

OTHER PUBLICATIONS

Notice of Opposition to a European Patent (EP 1 811 013) filed by DEB Worldwide Healthcare Inc. against Gojo Industries dated May 12, 2010.
Complaint for Correction of Inventorship of Patent; Case 1:10-CV-00266-GMS, filed Apr. 2, 2010 in the United States District Court for the District of Delaware.
Worldwide Healthcare, Inc., "Material Safety Data Sheet", Jan. 24, 2007.
U.S. Office Action mailed Apr. 30, 2007 for U.S. Appl. No. 11/799,042.
Office Action from the Chinese Patent Office (translation) dated Aug. 25, 2010 for Application No. 200680015637.1.
Response to Canadian Patent Office dated May 26, 2010 for Application No. 2,540,085.
Amendments submitted to EPO dated May 26, 2010 for Application No. 06705273.8.
Response to the Australian Patent Office dated Mar. 23, 2010 for Application No. 2004275900.
Response to the Canadian Patent Office dated Mar. 18, 2010 for Application No. 2,595,025.
Amendment filed with the New Zealand Patent Office dated Dec. 21, 2009 for Application No. 561741.
Response to the Canadian Patent Office dated Dec. 22, 2009 for Application No. 2,540,085.
Response to the New Zealand Patent Office dated Nov. 19, 2009 for Application No. 561741.
Response to Canadian Patent Office dated Nov. 10, 2009 for Application No. 2,595,025.
Office Action from the Ukranian Patent Office (translation) dated Jul. 30, 2009 for Application No. a 200710192/M.
Office Action dated May 10, 2011 in U.S. Appl. No. 12/878,786.
Office Action dated May 10, 2011 in U.S. Appl. No. 12/878,793.
Office Action dated Apr. 29, 2011 in U.S. Appl. No. 12/552,126.
Office Action dated Mar. 25, 2011 in U.S. Appl. No. 12/624,073.
Communication dated Mar. 9, 2011 in the opposition to European Patent 1 811 013.
Amendment dated Feb. 23, 2011 in U.S. Appl. No. 12/179,410.
Amendment and Response dated Feb. 18, 2011 in U.S. Appl. No. 12/878,786.
Amendment and Response dated Feb. 18, 2011 in U.S. Appl. No. 12/878,793.
Amendment and Response dated Feb. 18, 2011 in U.S. Appl. No. 12/552,126.
Office Action dated May 24, 2011 in U.S. Appl. No. 12/179,410.
Office Action dated Feb. 15, 2011 in U.S. Appl. No. 11/806,767.
Request for Certificate of Correction for US Patent No. 7,651,990 (U.S. Appl. No. 11/151,563) mailed Jun. 20, 2011.
Communication dated Jun. 20, 2011 in European Application No. 06 772 279.3.
Communication dated Apr. 26, 2010 in European Application No. 04786634.8.
Response to Office Action and Amendments dated Oct. 7, 2010 for Canadian Application No. 2,595,025.
Communication dated Jan. 1, 2010 in European Application No. 04786634.8.
Office Action dated Apr. 13, 2011 in U.S. Appl. No. 11/520,819.
Appellant's Brief on Appeal dated Jun. 13, 2011 in U.S. Appl. No. 11/075,287.
Appellant's Brief on Appeal dated Jun. 14, 2011 in U.S. Appl. No. 11/369,381.
Reply from Australian Patent Office dated Jun. 1, 2010 for Application No. 2005318384.
EP 1 233 749 issued Nov. 21, 2000, Biering, Holger (English-language claims).
Brochure, Polyox Water-Soluble Resins, Nordmann, Rassmann GmbH, Hamburg, Germany, Dec. 16, 2004 or earlier.
DE 10 2004 062 775 A1 filed on Dec. 21, 2004 (Certified translation).

The Dow Chemical Company Sales Specification for Specified Material 00029789-S: Ethocel Standard 100 Industrial Ethylcellulose printed Sep. 11, 2001.
The Dow Chemical Company Sales Specification for Specified Material 00116267-S: Ethocel Standard 300 Industrial Ethylcellulose printed Sep. 11, 2001.
The Dow Chemical Company Sales Specification for Specified Material 00129064-S: Polyox™ WSR N10 Amerchol printed Feb. 28, 2003.
The Dow Chemical Company Sales Specification for Specified Material 00129042-S: Polyox™ WSR N3000 Amerchol printed Feb. 18, 2003.
The Dow Chemical Company Sales Specification for Specified Material 00126141-S: Polyox™ WSR N60K printed Feb. 18, 2003.
Toxicological Test Results From Literature, Final Report of the Safety Assigment of Dimethicone Copolyol, Journal of American College of Toxicology, vol. 1, No. 4, 1982 dated Jul. 30, 2001 (Goldschmidt Personal Care—Degussa).
Floyd, et al., "Performance-Drive: New Silicone Copolymers," Global Cosmetics Industry, Sep. 2000.
Degussa Creating Essentials, Product Data Record for ABIL® B 8832 (3 pages) dated Jul. 14, 2004, Mat. No. 202534, Edition 1.
Degussa, Product Specification for ABIL® B 8832 (1 page) dated Aug. 26, 2004 (printed Sep. 6, 2004), Spec. No. ST-980121.
Degussa, Summary of toxicological and ecotoxicological data for ABIL® B 8832 (3 pages) dated May 17, 2002.
Dow PowerPoint Presentation entitled: "METHOCEL Applications in Personal Cleansing, a Superior Sensory Experience", Dec. 9, 2004 or earlier.
Dow PowerPoint Presentation entitled: ETHOCEL General Properties (15 pages, Dec. 9, 2004 or earlier).
Response to the Chinese Patent Office dated May 18, 2011 in Application No. 200680015637.1.
Office Action dated Apr. 11, 2011 in U.S. Appl. No. 11/806,767.
Office Action dated Apr. 15, 2011 in U.S. Appl. No. 10/591,243.
Office Action dated May 26, 2011 in US Application No. 12/659,063.
Deb Worldwide Healthcare Inc. and Deb Canadian Hygiene Inc., Plaintiffs, and Ecolab Co., Defendant, Court File No. T-379-11, Deb's Statement of Claim dated Mar. 7, 2011.
Deb Worldwide Healthcare Inc. and Deb Canadian Hygiene Inc., Plaintiffs, and Ecolab Co., Defendant, Court File No. T-379-11, Ecolab's Statement of Defense and Counterclaim dated Jun. 3, 2011.
Deb Worldwide Healthcare Inc. and Deb Canadian Hygiene Inc., Plaintiffs, and Ecolab Co., Defendant, Court File No. T-379-11, Deb's Reply and Defence to Counterclaim dated Jul. 11, 2011.
Deb Worldwide Healthcare Inc. and Deb Canadian Hygiene Inc., Plaintiffs, and Ecolab Co., Defendant, Court File No. T-379-11, Ecolab's Reply to Defence to Counter dated Jul. 11, 2011.
Deb Worldwide Healthcare Inc., Applicants and Kimberly-Clark Australia Pty. Ltd., No. VID 295 of 2011, Statement of Cross-Claim dated Aug. 2, 2011 (Federal Court of Australia, District Victoria, General Division).
Deb Worldwide Healthcare Inc., Applicants and Kimberly-Clark Australia Pty. Ltd., No. VID 295 of 2011, Notice of Filing, Statement of Claim and Certificate of Legal Representation dated Apr. 18, 2011 (Federal Court of Australia, District Victoria, General Division).
Amendment in U.S. Appl. No. 12/624,073, filed Jul. 29, 2011.
Amendment in U.S. Appl. No. 12/787,624, filed Jul. 19, 2011.
Notice of Allowance in U.S. Appl. No. 12/787,624 mailed on Aug. 5, 2011.
Communication in European Application No. 06 772 279.3-2108 dated Jun. 20, 2011.
Office Action dated May 13, 2011 in U.S. Appl. No. 12/787,624.
Acknowledgement of documents and Summons to Attend Oral Proceedings dated Sep. 9, 2011 for EP Patent No. 18110130.
Translation of Communication from the European Patent Office in Veeger et al, EP 05 825 981.3 (counterpart to U.S. Appl. No. 12/624,073).
Office Action dated Oct. 26, 2011 in U.S. Appl. No. 11/075,287, filed Mar. 8, 2005.
Appellant's Brief on Appeal dated Oct. 31, 2011 in U.S. Appl. No. 12/179,410, filed Jul. 24, 2008.

(56) References Cited

OTHER PUBLICATIONS

Office Communication from the US Patent Office dated Oct. 21, 2011 in U.S. Appl. No. 11/806,767, filed Jun. 4, 2007.
Office Communication from the US Patent Office dated Oct. 21, 2011 in U.S. Appl. No. 11/520,819, filed Sep. 14, 2006.
Translation of International Preliminary Report on Patentability from International Application No. PCT/EP2005/013742 dated Sep. 20, 2007.
Wang, et al., "Direct Force Measurement of Comb Silicone Surfactants in Alcoholic Media by Atomic Force Microscopy", Journal of Colloid and Interface Science 242, 337-345 (2001).
Prieto et al., "Structure-function relationships of dimethicone copolyol", j. Cosmet. Sci., 51, 91-101 (Mar./Apr. 2000).
Japanese Patent Application No. 2008-500017, Drafting Date: May 26, 2011, Mailing Date: May 31, 2011 "Notice of Reasons for Rejection".
Japanese Publication No. 06-327750 published Nov. 29, 1994, "English Abstract of Reference 2".
Gojo submission of Feb. 15, 2012 in the Opposition to European Patent No. 1 811 013 B1 (including Auxiliary Claim Sets).
Declaration of Evan Hillman and Annexes submitted in the Opposition to European Patent No. 1 811 013 B1.
Declaration of Amanda J. Copeland and Annexes submitted in the Opposition to European Patent No. 1 811 013 B1.
Submission by Deb Worldwide Healthcare, Inc. in the Opposition to European Patent No. 1 811 013 B1 (including Exhibit E).
Reply dated Dec. 30, 2011 to the European Patent Office Communication dated Jun. 20, 2011 by 3M regarding 06 77 2279.3, including an Amended set of claims (marked-up and clean copy) and Acknowledgment of receipt.
Examiner's Answer mailed Feb. 9, 2012 to Appeal Brief filed Jul. 18, 2011 for U.S. Appl. No. 11/369,381.
Request for Oral Hearing filed Feb. 8, 2012 in U.S. Appl. No. 12/179,410.
Amendment and Response dated Feb. 12, 2007 in U.S. Appl. No. 11/340,778.
Amendment and Response dated Sep. 11, 2008 in U.S. Appl. No. 11/340,778.
Preliminary Amendment dated Aug. 22, 2006 for U.S. Appl. No. 11/507,626.
Notice of Reasons for Rejection for Canadian Patent Application No. 2008-500017 mailed Jan. 17, 2012.
Mason Chemical Company, brochure for Masurf FS-115/FS-130 100504.
Decision in the Opposition to European Patent No. 1 811 013 B1 (including Auxiliary Requests) dated Apr. 10, 2012.
Notice of Reasons for Rejection for Canadian Patent Application No. 2008-500017 mailed May 31, 2011.
http://www.ipc.bas.bg/book1.htm (webpage regarding Exerowa et al., Foam and Foam Films; Theory, Experiment, Application, published by Elsevier (Dec. 1997)).
Amendment and Response filed Oct. 31, 2007 in U.S. Appl. No. 10/400,597.
Amendment and Response and Request for Reconsideration filed Jun. 2, 2008 in U.S. Appl. No. 11/312,559.
Interview Summary mailed Apr. 23, 2008 in U.S. Appl. No. 11/312,559.
Non-final rejection mailed Feb. 20, 2008 in U.S. Appl. No. 11/312,559.
Amendment and Response filed Jun. 22, 2007 in U.S. Appl. No. 11/312,559.
Non-final Rej~ction mailed Feb. 22, 2007 in U.S. Appl. No. 11/312,559.
S.C. Crema et al., "Foaming of Anhydrous Methanol for Well Stimulation", Society of Petroleum Engineers, SPE 13565, (1985).
Paul A. Sanders, "Aqueous Alcohol Aerosol Foams", Drug & Cosmetic Industry, XP000960450, vol. 99, No. 2, 1966, pp. 56, 58, 60,142,143,146-154.
Amendment and Response filed Apr. 18, 2008 in U.S. Appl. No. 11/561,563.
Non-final Rejection mailed Jan. 29, 2008 in U.S. Appl. No. 11/561,563.
Amendment and Response and RCE filed Nov. 13, 2007 in U.S. Appl. No. 11/561,563.
Advisory action mailed Oct. 1, 2007 in U.S. Appl. No. 11/561,563.
Amendment and Response filed Sep. 11, 2007 in U.S. Appl. No. 11/561,563.
Final Rejection mailed Jun. 11, 2007 in U.S. Appl. No. 11/561,563.
Amendment and Response filed Mar. 19, 2007 in U.S. Appl. No. 11/561,563.
Non-final rejection mailed Oct. 19, 2006 in U.S. Appl. No. 11/561,563.
Amendment and Response filed Oct. 31, 2007 in U.S. Appl. No. 11/340,778.
Non-Final Rejection mailed Jan. 3, 2006 in U.S. Appl. No. 10/992,494.
Amendment and Response filed Jul. 3, 2006 in U.S. Appl. No. 10/992,494.
Non-final Rejection mailed Sep. 26, 2006 in U.S. Appl. No. 10/992,494.
Amendment and Response and RCE filed Mar. 26, 2007 in U.S. Appl. No. 10/992,494.
Non-final rejection mailed Apr. 9, 2007 in U.S. Appl. No. 10/992,494.
Final Rejection mailed May 7, 2007 in U.S. Appl. No. 11/048,031.
Non-final rejection mailed May 11, 2006 in U.S. Appl. No. 11/048,031.
Amendment and Response filed Aug. 11, 2006 in U.S. Appl. No. 11/048,031.
Final Rejection mailed Feb. 11, 2008 in U.S. Appl. No. 11/048,040.
Amendment and Response filed Nov. 29, 2007 in U.S. Appl. No. 11/048,040.
Notice of Non-Compliant Amendment mailed Oct. 29, 2007 in U.S. Appl. No. 11/048,040.
Amendment and Response filed Oct. 16, 2007 in U.S. Appl. No. 11/048,040.
Non-final Rejection mailed Jul. 16, 2007 in U.S. Appl. No. 11/048,040.
Amendment and Response filed Jun. 11, 2007 in U.S. Appl. No. 11/048,040.
Notice of Non-Compliant Amendment mailed Jun. 1, 2007 in U.S. Appl. No. 11/048,040.
Amendment and Response and RCE filed May 21, 2007 in U.S. Appl. No. 11/048,040.
Final Rejection mailed Nov. 20, 2006 in U.S. Appl. No. 11/048,040.
Amendment and Response filed Sep. 5, 2006 in U.S. Appl. No. 11/048,040.
Non-final Rejection mailed Jul. 18, 2006 in U.S. Appl. No. 11/048,040.
Final Rejection mailed Jul. 9, 2008 in U.S. Appl. No. 11/561,563.
Final rejection mailed Sep. 19, 2008 in U.S. Appl. No. 11/312,559.
Complaint. *3M Company and 3M Innovative Properties Company v. Gojo Industries, Inc.* United States District Court for the District of Minnesota. Case No. 0:10cv04065. Filed Sep. 28, 2010.
Response to Opposition (European Patent Application No. 06256249.1/European Patent No. EP 1 811 013) as filed by Ecolab, Inc. by Gojo Industries, Inc. dated Dec. 20, 2010.
U.S. Office Action mailed Jan. 19, 2011 for U.S. Appl. No. 11/075,287, filed Mar. 8, 2005.
U.S. Office Action mailed Jan. 19, 2011 for U.S. Appl. No. 11/369,381, filed Mar. 7, 2006.
Protest Under 37 C.F.R. 1.291 electronically filed on Dec. 20, 2010 for U.S. Appl. No. 12/878,786, filed Sep. 9, 2010.
U.S. Office Action mailed Dec. 13, 2010 for U.S. Appl. No. 12/878,786, filed Sep. 9, 2010.
Protest Under 37 C.F.R. 1.291 electronically filed on Dec. 20, 2010 for U.S. Appl. No. 12/878,793, filed Sep. 9, 2010.
U.S. Office Action mailed Dec. 10, 2010 for U.S. Appl. No. 12/878,793, filed Sep. 9, 2010.
U.S. Office Action mailed Dec. 13, 2010 for U.S. Appl. No. 12/552,126, filed Sep. 1, 2009.
Amendment electronically filed on Nov. 2, 2010 for U.S. Appl. No. 11/075,287, filed Mar. 8, 2005.

(56) References Cited

OTHER PUBLICATIONS

Response in European Patent Application No. 08250626.2 in the name of Gojo Industries, Inc. dated Dec. 12, 2009.
Supplemental Response and Amendment electronically filed on Aug. 13, 2010 for U.S. Appl. No. 12/032,083, filed Feb. 15, 2008.
U.S. Office Action mailed Aug. 3, 2010 for U.S. Appl. No. 11/075,287, filed Mar. 8, 2005.
U.S. Office Action mailed Aug. 3, 2010 for U.S. Appl. No. 11/369,381, filed Mar. 7, 2005.
Information Disclosure Statement electronically filed on Nov. 19, 2010 for U.S. Appl. No. 12/624,073, filed Nov. 23, 2009.
U.S. Office Action mailed Nov. 23, 2010 for U.S. Appl. No. 12/179,410, filed Jul. 24, 2008.
Myers, D., "Surfactant Science and Technology", selected pages, 1992, 2nd ed., VCH Publishers, Inc. New York, NY.

* cited by examiner

HIGH ALCOHOL CONTENT FOAMING COMPOSITIONS COMPRISING AN ANIONIC PHOSPHATE FLUOROSURFACTANT

CROSS REFERENCE TO RELATED U.S. APPLICATIONS

This patent application is a continuation of U.S. application Ser. No. 12/659,063, filed Feb. 24, 2010, which is a divisional application of U. S. patent application Ser. No. 11/507,626 filed on Aug 22, 2006, which issued as U.S. Pat. No. 7,683,018 on Mar 23, 2010, which was a continuation of U.S. patent application Ser. No. 10/952,474 filed on Sep. 29, 2004, which issued as U.S. Pat. No. 7,199,090 on Apr. 3, 2007, and which relates to, and claims the priority benefit from, U.S. Provisional Patent Application No. 60/506,172 filed on Sep. 29, 2003, and U.S. Provisional Patent Application No. 60/591,601 filed on Jul. 28, 2004, all of which are incorporated herein by reference in their entireties.

FIELD OF THE INVENTION

The present invention relates to compositions with high contents of lower alcohol ($C_{1-4}$) that could be a gel-like composition or a solution able to be dispensed as a foam. The compositions to be dispensed as foams contain a fluorosurfactant and when mixed with air provide a stable alcohol foam which can be used for personal cleaning or for disinfecting purposes. The gel-like compositions may or may not contain a fluorosurfactant.

BACKGROUND ART

Ethanol and/or Isopropyl alcohol compositions with at least 60% percent v/v (approximately 52% by weight) are well known to be antibacterial, therefore widely accepted for disinfecting purposes. Nonetheless due to the inherent characteristics of alcohol, it is perceived that the higher the content the better the product and a higher than 60% by volume alcohol content solution is more desirable.

Alcohol disinfectant solutions are generally thickened in order to eliminate the waste and facilitate spreading the composition throughout the desired area. It is also known that other than gelling agents one can use paraffin or waxes to achieve thickening of a solution with high alcohol concentration. Such a composition added with lanolin to reduce the melting point closer to body temperature is described in U.S. Pat. No. 2,054,989. One of the disadvantages of gels and such type thick alcohol containing compositions is that if they do not leave a tacky feeling on the hands after one use (although some do), the effect builds up after repetitive use during the day, making it necessary to eventually wash off the thickeners before continuing the usage of an alcohol antiseptic solution. The present invention if formulated for such type of product does not leave such a feel, and does not need to be washed off after having been used repeatedly.

Another way of thickening high alcohol content solutions has also been taught in U.S. Pat. Nos. 6,090,395 and 6,623,744 where they use emulsifiers and surfactants as the thickening system to produce a hydroalcoholic lotion with a viscosity of at least 4,000 cps. Also, U.S. Pat. No. 4,956,170 discloses polyethoxylated non-ionic surfactants/emulsifiers to stabilize the added emollient oils in addition to a fatty alcohol although with the addition of a polymeric thickening agent to prepare a hydroalcoholic skin moisturizing/conditioning antimicrobial gel. The disinfecting compositions of the present invention that are gel-like have a viscosity lower than 4,000 cps and no polymeric thickening agent is added.

Generally speaking a high alcohol content disinfectant solution disinfects but does not clean. In order to make them disinfect and clean, so much soap would be needed that the skin would feel soapy and disagreeable, unacceptable for rubbing alcohol purposes. Nonetheless, a non-irritant skin disinfecting high lower alcohol content formulation for use as a skin-washing agent is successfully attained by combining emulsifiers, surfactants and skin emollients to be used as a gel or ointment as described in U.S. Pat. No. 5,629,006.

Surfactants other than for cleaning purposes are also used for spreading an aqueous composition containing one or more active substances rapidly and evenly over a surface due to their wetting properties. The use of good wetting agents definitely improves the efficient use of active substances in different compositions as described in U.S. Pat. No. 5,928,993. Hence, the composition described in the present invention includes the addition of surfactants, specifically fluorosurfactants which are well known for their unparalleled wetting power and which are also surface-active in the lower alcohols used as disinfectant and solvent system in levels which make it acceptable even for rubbing alcohol purposes, providing cleaning, wetting and foaming properties to the composition.

Although a high alcohol content disinfectant solution has good disinfectant characteristics, it has a sharp smell and is generally perceived to cause drying of the skin, characteristics which can also be diminished to a desirable level in the present invention.

A greater than 40% v/v alcohol foam product, easy and safe to use, is desirable over conventional gel or ointment type composition products. The concentration of alcohol already poses a hazard in itself, and there are many applications in which the perceived risk may be diminished if it could be dispensed as a foam without the use of pressurized aerosol containers. A foam intended to be useful as a skin disinfecting agent must have a uniform consistency, spreadability, cleansing ability, and have a pleasant feel, i.e. have rapid breaking power when pressure is applied; all of which present a challenge for a high lower alcohol content composition.

The description of an aqueous foaming skin disinfecting composition using 15% w/w alcohol as a co-solvent, which requires no pressurized container or added propellant to produce the foam, is described in U.S. Pat. No. 3,962,150.

The foam-forming agents utilized heretofore, have been incapable of forming stable foams when the liquid phase has high alcohol content without using other ingredients. Furthermore, lower alcohols have been considered to be defoamers rather than foam-promoting chemicals. According to Klausner, in U.S. Pat. No. 3,131,153, if more than 64% alcohol is used non-homogeneous compositions are obtained. The compositions in the patent required propellant to foam and the foams produced were of limited stability.

Prior to this invention, when a greater than 40% v/v alcohol concentration is required in a product, it is generally accepted that the product will be either liquid or gel, and that if a foam is desired then the concentration of alcohol would need to be reduced or the use of a propellant and a pressurized system would be required.

Surprisingly, in the few "foamable" high alcohol content products disclosed, the types of foam obtained were not similar to those expected from aqueous solutions. The foams obtained are described as fast or aerated foam, quick breaking, with low or limited stability, which would not last for more than one minute, being generally gone within seconds.

It has been disclosed that fluorosurfactants and alcohol can be combined to produce a "stable" foam by a process using high-pressurized means to generate the foam. Highly stable pressurized foams containing high lower alcohol contents and methods of forming and using such pressurized foams in the oil industry using a non-ionic surfactant or mixture of non-ionic surfactants of a specific group of fluorosurfactants are provided in U.S. Pat. No. 4,440,653. The compositions in this patent require the use of a pressurized gas system to generate the foam.

Various examples of compositions with a high lower alcohol content that are dispensed as a foam have been described, although for the purpose of the present invention the characteristics of the foam are not of the desired outcome, since they are fast breaking, of low stability and the foam is produced by means of propellants and aerosol containers only, as the one described in U.S. Pat. No. 5,906,808, which discloses a product that uses an emulsifying wax NF, and a combination of stearyl and cetyl alcohol, or other wax combinations, which improve the foaming performance of the composition, in combination with cetyl lactate, to produce a 0.8% chlorhexidine gluconate alcohol product.

U.S. Pat. No. 5,167,950 issued to Lins discloses a foam product which requires a propellant and no surfactant is added as a cleaning agent. The composition disclosed in this patent is based upon using an emulsifier system (fatty alcohol ROH 16-22 carbons) in combination with the use of a thickening agent (carbomer, klucel, etc.).

U.S. Pat. No. 5,167,950 to Lins discloses an antimicrobial aerosol mousse having a high alcohol content. The mousse comprises alcohol, water, a polymeric gelling agent and a surfactant system comprising a C16-C22 alcohol, aerosol propellant and a non-ionic polyethoxylated surfactant. Despite the work done to date it has been shown that there is little specific knowledge on how foams react and are formed, and surprisingly formulations that might seem not foamable result in the best foam producing ones while other formulations which seemed to have been producing foam even while being prepared did not perform well at all in some non-aerosol foam dispensers. The behaviour of aqueous foams is not the same of that of an alcohol foam.

The traditional ways of forming a gel using polymeric thickeners presents undesirable characteristics and similarly little has been done in forming emulsion-like thickened gels.

It would be very advantageous to have alcohol based disinfecting formulations which may be dispensed as either a gel or a foam. Further, it would be very advantageous and desirable to find a foaming agent that could be used in concentrations that would allow it to be used in products that can remain in the area on which they have been applied and do not need to be rinsed or wiped off due to small amounts of residue remaining after evaporation. Thus it would also be very advantageous to provide foams or gels that do not leave an unpleasant sticky after-feel as most commercial alcohol gel products are known to, or which clog up the dispensing equipment used to dispense the foams and gels.

SUMMARY OF THE INVENTION

It is an object of this invention to provide high alcohol content liquid compositions, which contain a surfactant/cleaning agent as well as a disinfectant/cleaning/solvent/carrier and that causes very little drying to the skin or the hands of the user and is able to be dispensed either as a gel or as a foam from both pressurized and non-pressurized systems.

The present invention provides high alcohol content compositions that are either gels or able to be dispensed as a foam, which are readily spread over the desired surface. Amongst the different applications where such compositions might be of use, it is another object to also provide an antimicrobial alcohol foam and an antimicrobial alcohol gel. The foamable compositions when dispensed from a suitable dispenser are stable and do not require the use of propellants and pressurized containers. The gels disclosed herein with a viscosity of less than 4,000 cps do not use the gelling or thickening agents typically used in commercial gels and therefore after single or multiple applications of the gel there is not the usual tacky or sticky after-feel and the gel does not clog the dispensers from which the gels are dispensed.

These and other objects and advantages will be apparent from the following description of the invention. All percentages provided herein are based on the total weight unless otherwise indicated.

Accordingly, the present invention provides compositions for personal hygiene, as follows.

Foamable Compositions

The present invention provides a foamable alcohol composition, comprising:

a) an alcohol $C_{1-4}$, or mixtures thereof, present in an amount greater than about 40% percent v/v of the total composition;

b) an effective fluorinated surface active agent for foaming, which is physiologically acceptable for skin disinfecting, present in an amount of at least 0.001% weight percent of the total composition such that the composition foams under low pressure conditions; and c) water present in an amount to balance the total composition to 100% by weight.

In this aspect of the invention the effective fluorinated surface active agent is present in an amount from about 0.001% to about 10.0% weight percent of the total composition which is physiologically acceptable so it can be used in personal care type products.

In a preferred embodiment of the invention the fluorosurfactant may be an amphoteric polytetrafluoroethylene acetoxypropyl betaine of the following formula, $(CF_3CF_2(CF_2CF_2)_nCH_2CH_2(OAc)CH_2N+(CH_3)_2CH_2COO-)$ where n=2 to 4, an ethoxylated nonionic fluorosurfactant of the following structure: $RfCH_2CH_2O(CH_2CH_2O)xH$ where $Rf=F(CF_2CF_2)y$, x=0 to about 15 and y=1 to about 7; or an anionic phosphate fluorosurfactant of the following structure: $(RfCH_2CH_2O)xP(O)(ONH_4)y$ where $Rf=F(CF_2CF_2)z$, x=1 or 2, y=2 or 1 and z=1 to about 7, or mixtures thereof.

The present invention also provides a foamable, alcohol disinfecting composition, comprising:

a) an alcohol $C_{1-4}$ or mixtures thereof, present in an amount between about 60% to above 80% v/v of the total composition;

b) a physiologically acceptable fluorosurfactant present in an amount from about 0.01% to about 2.0% by weight of the total composition such that the foamable alcohol disinfecting composition foams under low pressure conditions when dispensed from an unpressurized container;

c) a foam stabilizing agent present in an amount from about 0.01 to about 12.0% by weight;

d) any one of moisturizers, emollients and combinations thereof present in an amount from about 0.05 to about 5.0% by weight; and e) water in an amount to balance the total compositions to 100% by weight.

In another aspect of the invention there is provided an alcohol disinfecting composition, comprising;

a) ethanol present in an amount between about 60% to 70% percent v/v of the total composition;

b) a physiologically acceptable fluorosurfactant in an amount from about 0.01% to about 2.0% weight percent of the total composition;

c) at least one nonionic surfactant selected from the group consisting of polyethoxylated fatty alcohols present in an amount from about 0.01 to about 10.0% weight percent;

d) a foam stabilizing agent;

e) water in an amount to balance the total composition to 100% weight percent.

The present invention also provides an alcohol disinfecting composition comprising:

a) ethanol present in an amount between about 60% to 70% percent v/v of the total composition;

b) a physiologically acceptable anionic phosphate fluorosurfactant in an amount from about 0.01% to about 2.0% weight percent of the total composition;

c) at least 1% n-propanol;

d) foam stabilizing agents that at least include 1,3-Butyleneglycol % 2, Butoxyethanol in 0.001-3% ea;

e) a lipid layer enhancer such as a mixture of alkylglucoside and glyceryl oleate; and f) water in an amount to balance the total composition to 100% weight percent.

Gel-Like Compositions

In this aspect of the invention there is provided an alcohol gel-like composition, comprising;

a) an alcohol $C_{1-4}$, or mixtures thereof, present in an amount greater than about 40% percent v/v of the total composition;

b) at least one nonionic surfactant selected from the group consisting of a poly(ethoxylated and/or propoxylated)alcohol, a poly(ethoxylated and/or propoxylated)ester, a derivative of a poly(ethoxylated and/or propoxylated)alcohol, a derivative of a poly(ethoxylated and/or propoxylated)ester, an alkyl alcohol, an alkenyl alcohol, an ester of a polyhydric alcohol, an ether of a polyhydric alcohol, an ester of a polyalkoxylated derivative of a polyhydric alcohol, an ether of a polyalkoxylated derivative of a polyhydric alcohol, a sorbitan fatty acid ester, a polyalkoxylated derivative of a sorbitan fatty acid ester, and mixtures thereof, present in an amount between about 0.10% to about 5% weight percent;

c) an emulsifier present in an amount between about 0.10% to about 3.0% weight percent; and d) water in an amount sufficient to form a stable gel-like disinfecting composition The compositions disclosed herein provide a wide variety and range of high alcohol content disinfecting products. According to the percentage of alcohol used in the compositions and by varying the proportions of the other constituents in the formulation, foams with differing properties can be achieved thereby allowing the production of foams that are either coarse or wet which quickly flatten, or foams that are soft which contain fine bubbles and which are relatively dry having long foam stability, or creamy thick foams that are gel-like. Also, the compositions may or may not be disinfecting according to the percentage of alcohol.

It was surprisingly found that by varying the percentages of the ingredients an alcohol gel-like composition was obtained which did not dry the hands or leave a sticky after-feel and that did not clog the gel dispensers, having the desired consistency and showing a viscosity of less than 4,000 cps.

Some of the compositions can conveniently be manufactured in a two step process such that most of the alcohol can be added at a later time and/or location making it the first part a desirable concentrate suitable for shipping less hazardous goods and weight. Warming the first part from 30 to 80 degrees Celsius, (depending on the particular composition) before adding the major portion of alcohol improves the long term stability of the compositions. This warming can either take place the same day in the same location where the finished composition is prepared or the concentrate first part can be stored or shipped elsewhere and the warming can take place either when the first part is mixing or right before adding the major portion of alcohol.

It should be evident that the described embodiment can be subjected to adjustment and/or improvement for specific applications either as a gel or a foam or to contain a desired active ingredient, without departing from the scope of the present invention. Different materials and/or ingredients will be then needed to compensate for the composition and/or foam stability disruption that might be generated by the change (i.e. introducing a more compatible secondary or even primary surfactant, adjusting the compatible foam stabilizer percentage and/or varying the relative amount of emulsifier and/or alcohol or water) or to compensate for shifts in desired viscosity and foam characteristics to obtained the desired gel (i.e. reduce the amount of fluorosurfactant or increase the polyethoxylated surfactants, or add an emulsifier and/or increase or decrease alcohol and/or water). These and other changes may be made in the details within the spirit of the invention, which is to be broadly construed and not to be limited except by the character of the claims appended hereto.

For example, the alcohol based compositions may contain up to 10% by weight of other active ingredients or additives or combinations thereof commonly added to aerosol compositions or to toiletries, cosmetics, pharmaceuticals, etc. Materials that may be added may include organic gums and colloids, lower alkanolamides of higher fatty acids, short chain diols and/or triols, alkylglucosides, fragrance, coloring matter, additional emollients, ultraviolet absorbers, solvents, emulsifiers, foam stabilizers or mixture of such stabilizers, suspending agents, buffers, conditioning agents, antioxidants, bactericides, medicinal active ingredient, and the like.

The present invention provides a composition, comprising;

a) an alcohol $C_{1-4}$, or mixtures thereof, present in an amount greater than about 40% v/v of the total composition;

b) at least one nonionic surfactant selected from the group consisting of a poly(ethoxylated and/or propoxylated)alcohol, a poly(ethoxylated and/or propoxylated)ester, a derivative of a poly(ethoxylated and/or propoxylated)alcohol, a derivative of a poly(ethoxylated and/or propoxylated)ester, an alkyl alcohol, an alkenyl alcohol, an ester of a polyhydric alcohol, an ether of a polyhydric alcohol, an ester of a polyalkoxylated derivative of a polyhydric alcohol, an ether of a polyalkoxylated derivative of a polyhydric alcohol, a sorbitan fatty acid ester, a polyalkoxylated derivative of a sorbitan fatty acid ester, and mixtures thereof, present in an amount between about 0.10% to about 5% weight percent c) an emulsifier present in an amount between about 0.10% to about 3.0% weight percent; and d) water in an amount sufficient to form a stable gel-like composition with a viscosity less than 4,000 cps.

The present invention also provides a method of forming a skin-disinfecting foam containing alcohol, comprising the steps of:

combining an alcohol $C_{1-4}$, or mixtures thereof, present in an amount greater than about 60% v/v of the total composition with a physiologically acceptable effective fluorinated surface active agent for foaming present in an amount of at least 0.001% by weight percent of the total composition, and water present in an amount to balance the total composition to 100% by weight to form an alcohol-fluorosurfactant mixture and storing said composition in an unpressurized dispenser having a dispenser pump; and activating the dispenser pump to combine the alcohol-fluorosurfactant mixture with air to form and dispense a skin disinfecting foam containing alcohol.

In another aspect of the invention there is provided a high-alcohol, foamable, skin-disinfecting composition, comprising:

a) an alcohol $C_{1-4}$, or mixtures thereof, present in an amount greater than about 60% v/v of the total composition;

b) water present in an amount to balance the total composition to 100% by weight; and c) a physiologically acceptable fluorinated surface active agent for foaming present in an amount of at least 0.001% by weight of the total composition such that the composition has a surface tension less than 20 dynes/cm.

The present invention also provides a high-alcohol, foamable, skin-disinfecting composition, comprising:

a) an alcohol $C_{1-4}$, or mixtures thereof, present in an amount greater than about 60% v/v of the total composition;

b) water present in an amount to balance the total composition to 100% by weight; and c) a physiologically acceptable fluorinated surface active agent for foaming present in an amount of at least 0.001% by weight of the total composition such that the composition foams without the use of propellants or pressurized containers.

The present invention also provides a method for personal disinfecting comprising:

applying to a person's skin a skin-disinfecting alcohol foam composition which comprises a) air mixed under low pressure conditions with b) a liquid comprising i) an alcohol $C_{1-4}$, or mixtures thereof, present in an amount greater than about 60% v/v of the total composition;

ii) water present in an amount to balance the total composition to 100% by weight; and iii) a physiologically acceptable effective fluorinated surface active agent for foaming present in an amount of at least 0.001% by weight of the total composition.

The present invention also provides a method for producing, and applying to a person's skin, a skin-disinfecting alcohol foam composition, comprising a) combining an alcohol $C_{1-4}$, or mixtures thereof, present in an amount greater than about 60% v/v of the total composition with an effective physiologically acceptable fluorinated surface active agent for foaming present in an amount of at least 0.001% by weight of the total composition, and water present in an amount to balance the total composition to 100% by weight to form an alcohol-fluorosurfactant mixture and storing said composition in an unpressurized dispenser having a dispenser pump;

b) activating the dispenser pump to combine the alcohol-fluorosurfactant mixture with air to form and dispense a skin-disinfecting alcohol foam; and c) applying the skin-disinfecting alcohol foam to the person's skin.

The invention will be described in connection with various specific examples, which are intended to be illustrative rather than limiting. Nevertheless, the present invention lends itself to the preparation of a wide variety of products, and it is to be understood that other embodiments may be utilized and that changes may be made without departing from the scope of the invention.

DETAILED DESCRIPTION OF THE INVENTION

Definitions

The term "emollient" as used herein refers broadly to materials which are capable of maintaining or improving the moisture level, compliance, or appearance of the skin when used repeatedly.

The term "emulsifier" as used herein refers to surfactants or other materials added in small quantities to a mixture of two miscible liquids for the purpose of aiding in the formation and stabilization of an emulsion.

The phrase "emulsifying ingredients" as used herein is synonymous with emulsifier defined above.

The term "emulsion" as used herein refers to a colloidal dispersion of one liquid in another.

The term "surfactant" as used herein is the widely employed contraction for "surface active agents" which is the descriptive generic term for materials that preferentially adsorb at interfaces as a result of the presence of both lyophilic and lyophobic structural units, the adsorption generally resulting in the alteration of the surface or interfacial properties of the system.

The term "fluorosurfactant" as used herein refers to a fluorinated surface active agent which enables the composition in which it is contained to clean, wet and foam.

The phrase "foam stabilizer" as used herein refers to an additive that increases the amount or persistence of foam produced by a surfactant system.

The phrase "gel-like composition" as used herein refers to a hydroalcoholic solution with at least 40% v/v alcohol content, which is thickened by the use of emulsifiers and surfactant to have a viscosity greater than water and less than 4,000 cps.

The term "disinfect" as used herein means to destroy or reduce harmful microorganisms.

The present invention provides compositions with high contents of lower alcohol ($C_{1-4}$) able to be dispensed as a gel or a foam. The foamable compositions when mixed with air deliver a stable foam to provide an alcoholic liquid solution which can be used for personal cleaning or for disinfecting purposes and which breaks on pressure application such as when a user rubs their hands or when applied over a surface. The gel composition delivers a liquid of the appropriate consistency to be readily spread on the hands, yet without dripping off. This gel composition with at least 60% v/v alcohol provides an effective disinfectant that does not leave a tacky after-feel once the alcohol has evaporated and that is common to such alcohol gels which use thickeners and gelling agents that have been used commonly in the past during single or multiple applications. The gel composition does not easily clog the dispensers as common gel products do.

The alcohol used in the present invention is a lower hydrocarbon chain alcohol such as a $C_{1-4}$ alcohol. The preferred alcohol is chosen from ethanol, 2-propanol, or n-propanol, most preferably ethanol, well accepted by Health Care personnel as an adequate disinfectant at the right percentages. The invention anticipates that a single alcohol may be used or that a blend of two or more alcohols may comprise the alcohol content of the composition either for a gel-like or foamable product.

Foamable Compositions

One of the main achievements of the present invention is making compositions with a greater than 40% v/v alcohol content able to be dispensed as a cosmetically appealing foam. The other important achievement is to obtain an alcohol gel without using the typical gelling agents know to those skilled in the art which would not clog dispensers or leave a tacky after-feel.

The use of a fluorosurfactant is the key ingredient as the primary foaming agent in the compositions designed to foam disclosed herein. Fluorosurfactants have various interesting properties such as leaving little residue, being able to function in harsh chemical and thermal environments; they have an unparalleled wetting power, etc. Unlike traditional surfactants, they show unusual surface-active properties in organic solvents that are known to those skilled in the art, and that have made them widely used for applications in coatings, oilfield, material finishes, cleaning, paints, etc.

The fluorosurfactants suitable for these types of compositions may include, but are not limited to, ethoxylates, glycerol esters, amine oxides, acetylenic alcohol derivatives, carboxylates, phosphates, carbohydrate derivatives, sulfonates, betaines, esters, polyamides, silicones, and hydrocarbon surfactants that have been fluorinated and are compatible with the other components being used for a particular formulation.

A preferred fluorosurfactant is polytetrafluoroethylene acetoxypropyl betaine $CF_3CF_2(CF_2CF_2)nCH_2CH_2(OAc)CH_2N+(CH_3)_2CH_2COO—$, where n=2-4. However, it is contemplated that other fluorosurfactants may be used including as non-limiting examples for use in the present invention an ethoxylated nonionic fluorosurfactant of the following structure: $RfCH_2CH_2O(CH_2CH_2O)_xH$ where $Rf=F(CF_2CF_2)y$, x=0 to about 15 and y=1 to about 7; an anionic phosphate fluorosurfactant of the following structure: $(RfCH_2CH_2O)_xP(O)(ONH_4)_y$, where $Rf=(CF_2CF_2)z$, x=1 or 2, y=2 or 1, x+y=3, and z=1 to about 7 or mixtures thereof.

It was surprisingly found that despite the characteristics of fluorosurfactants, there was little or no information on their use to produce a foamable product with high alcohol content other than the one using non-ionic fluorosurfactants and pressurized gas as a foamer as taught in U.S. Pat. No. 4,440,653 incorporated herein by reference.

Furthermore, in order to obtain a high alcohol content product able to produce a foam even if no pressurized containers or propellants are used would require surface tension values as low as possible so that the pressure required to produce such foam by hand pumps and mechanical means would be sufficient. Hence, the lower than 20 dynes/cm (0.01% DW 25° C.) surface tension values achievable with these surfactants made them suitable for the application.

During the development of the present invention, it was unexpectedly found that a quick breaking aerated foam could even be obtained when using just ethanol and the fluorosurfactant, while using traditional surfactants at even double the percentage bore results that could not be even slightly similar and no foam at all could be obtained.

In order to achieve a commercially suitable formulation, reducing the amount of fluorosurfactant used while using the assistance of other ingredients such as secondary surfactants, emulsifiers, foam stabilizers, fragrances, and the like ingredients employed in cosmetics, aerosols, toiletries, personal care, etc. is one of the approaches followed. One of the commercial products obtained uses emulsifiers and polyethoxylated fatty acid surfactants disclosed in U.S. Pat. Nos. 5,167,950 and 6,090,395, both incorporated herein by reference, while other examples use a combination of different foam stabilizers to achieve a similar result.

Examples of secondary surfactants that may be used in the present compositions include alkylglucosides, a poly(ethoxylated and/or propoxylated)alcohol, a poly(ethoxylated and/or propoxylated)ester, a derivative of a poly(ethoxylated and/or propoxylated)alcohol, a derivative of a poly(ethoxylated and/or propoxylated)ester, an alkyl alcohol, an alkenyl alcohol, an ester of a polyhydric alcohol, an ether of a polyhydric alcohol, an ester of a polyalkoxylated derivative of a polyhydric alcohol, an ether of a polyalkoxylated derivative of a polyhydric alcohol, a sorbitan fatty acid ester, a polyalkoxylated derivative of a sorbitan fatty acid ester, a betaine, a sulfobetaines, imidazoline derivatives, aminoacid derivatives, lecithins, phosphatides, some amine oxides and sulfoxides and mixtures thereof, present in an amount between about 0.10% to about 5% weight percent.

A preferred betaine is cocamidopropyl betaine. A preferred alkylglucoside is cocoglucoside. Preferred polyethoxylated fatty alcohols are polyethoxylated stearyl alcohol (21 moles ethylene oxide) and polyethoxylated stearyl alcohol (2 moles ethylene oxide), and a combination of these two.

The compositions may include an antimicrobial agent. The following antimicrobials are offered as non-limiting examples of suitable antimicrobials for use in the present invention and may include chlorhexidine salt, iodine, a complexed form of iodine, parachlorometaxylenol, triclosan, hexachlorophene, a phenol, a surfactant having a long chain hydrophobic group and a quaternary group, hydrogen peroxide, silver, a silver salt, silver oxide, and mixtures thereof.

A preferred antimicrobial agent in the present compositions is chlorhexidine gluconate (CHG) present in an amount between about 0.50% to about 4.0% weight percent. Another preferred antimicrobial agent is didecyl dimethyl diamonium chloride in an amount between about 0.05% to 5% weight percent.

If the amount of ingredients employed is little enough not to leave a tacky feeling after the composition evaporates after single or multiple uses, and this is achieved while maintaining at least 60% v/v ethanol or n-propanol concentration or 70% v/v isopropanol, then the composition would be ideal for use as an alcohol hand sanitizer/disinfectant foamable composition.

The addition of water to the alcohol produces a more stable foam while allowing to reduce the amount of fluorosurfactant required to foam the product. For instance, using 0.5 to 1.0% fluorosurfactant with a 50 to 60% v/v alcohol water solution produces a stable foam that does not readily collapse and that produces a stable puff that does not fall even when inverted and does not collapse until pressure is applied (such as when rubbed in hands or on over a surface) to provide an alcoholic liquid solution.

The use of a mild non-irritant surfactant widely used in the cosmetic industry such as cocamidopropyl betaine as a secondary surfactant is more suitable to prepare the foamable hydroalcoholic composition of the present invention depending on the fluorosurfactant being used.

In order to stabilize the foam, foam stabilizers, as well as emulsifying ingredients have been tried with good results in allowing the product to be dispensed as a foam even when no propellant and/or pressurized container systems are used.

Examples of compatible foam stabilizers that can optionally be employed include lactic acid esters of monoglycerides, cationic emulsifiers, triquaternized stearic phospholipid complex, hydroxystearamide propyltriamine salts, lactic acid monoglycerides, food emulsifiers such as glyceryl monostearate, propylene glycol monostearate, sodium stearoyl lactylate, silicone wax, an encapsulated oil, Microcapsule Mineral Oil®.

A preferred foam stabilizer used in the present foamable compositions is cetyl betaine. A preferred combination of foam stabilizers is that of butyleneglycol, butoxyethanol and n-propanol.

Examples of moisturizers and/or emollients which may be used in the present formulations include lanolin, vinyl alcohol, polyvinyl pyrrolidone and polyols selected from the group consisting of glycerol, propylene glycol, glyceryl oleate and sorbitol, cocoglucoside or a fatty alcohol selected from the group consisting of cetyl alcohol, stearyl alcohol, lauryl alcohol, myristyl alcohol and palmityl alcohol, cetyl alcohol, ceteareth 20, and combinations thereof, present in an amount up to about 5%.

The compositions may include an acid or a base to adjust a pH of the composition to a pre-selected pH. The acid or base may present in an amount from about 0.05 to about 0.5% by weight of the total composition. Non-limiting examples of the acid used to adjust the pH include hydrochloric acid, citric acid and phosphoric acid, and a non-limiting example of the base used to adjust the pH includes sodium sesquicarbonate.

The compositions may also include a preservative in an amount from about 0.01 to about 5% by weight of the total composition.

The compositions formulated to be dispensed as a foam may be stored in an unpressurized dispenser having a dispenser pump for mixing the composition with air and dispensing foam therefrom. The composition may include an aerosol propellant in an amount from about 3 to about 20 weight percent of the total composition for pressurized discharge of the foam. The aerosol propellant may include propane, carbon dioxide, butane, dichloro difluoro methane, dichloro tetra fluoro ethane, octafluorocyclo butane; 1,1,1,2-tetrafluoroethane; 1,1,1,2,3,3,3 heptafluoropropane, and 1,1,1,3,3,3,-hexafluoropropane. When stored in a metal container with propellant, the formulation may include a corrosion inhibitor such as sorbic acid, benzoic acid, potassium sorbate and sodium benzoate, in an amount from about 0.1 to about 5 weight percent of the total composition.

Gel-Like Compositions

Some of compositions studied had some gel-like properties. This characteristic led to the second most important achievement of the present invention; that is an alcohol gel with viscosities less than 4,000 cps that do not use the conventional polymeric thickeners (i,e, cellulose derivatives, carbomers, etc) that are known to leave a sticky residue on surfaces on single and multiple applications that builds up. This discourages users and tends to clog the dispensers.

In order to prepare a gel-like composition, a fluorosurfactant is not required to form the gel, however, using a small amount improves the after-feel, it also allows one to reduce the usage of other surfactants required, therefore improving the performance of the composition. The use of the fluorosurfactant also noticeably improves the spreadability of the gel disinfecting compositions on the hands or a surface.

The following is a basic formulation of the gel-like compositions. An alcohol $C_{1-4}$, or mixtures thereof, present in an amount greater than about 40% v/v of the total composition, one or more nonionic surfactants present in an amount between about 0.10% to about 5% weight percent, an emulsifier present in an amount between about 0.10% to about 3.0% weight percent, and water in an amount sufficient to form a stable gel-like composition.

Non-limiting examples of non-ionic surfactants include poly(ethoxylated and/or propoxylated)alcohol, a poly(ethoxylated and/or propoxylated)ester, a derivative of a poly(ethoxylated and/or propoxylated)alcohol, a derivative of a poly(ethoxylated and/or propoxylated)ester, an alkyl alcohol, an alkenyl alcohol, an ester of a polyhydric alcohol, an ether of a polyhydric alcohol, an ester of a polyalkoxylated derivative of a polyhydric alcohol, an ether of a polyalkoxylated derivative of a polyhydric alcohol, a sorbitan fatty acid ester, a polyalkoxylated derivative of a sorbitan fatty acid ester, and mixtures thereof.

A preferred non-ionic surfactant includes polyethoxylated fatty alcohols such as polyethoxylated stearyl alcohol (21 moles ethylene oxide) and polyethoxylated stearyl alcohol (2 moles ethylene oxide), and/or a combination of polyethoxylated fatty alcohols.

To make the gel-like compositions for personal hygiene applications, the compositions may include a physiologically acceptable fluorinated surface active agent up to about 2.5%. A preferred fluorinated surface active agent is that used in the gel-like compositions, namely polytetrafluoroethylene acetoxypropyl betaine $CF_3CF_2(CF_2CF_2)nCH_2CH_2(OAc)CH_2N+(CH_3)_2CH_2COO—$, where $n=2-4$.

Another fluorinated surface active agent also preferred is an ethoxylated nonionic fluorosurfactant of the following structure: $RfCH_2CH_2O(CH_2CH_2O)_xH$ where $Rf=F(CF_2CF_2)y$, $x=0$ to about 15 and $y=1$ to about 7 and yet another one is an anionic phosphate fluorosurfactant of the following structure: $(RfCH_2CH_2O)_xP(O)(ONH_4)_y$, where $Rf=F(CF_2CF_2)z$, $x=1$ or 2, $y=2$ or 1, $x+y=3$, and $z=1$ to about 7 or mixtures thereof.

The following non-limiting examples are set forth to show for the various preferred embodiments and are not in any way to limit the scope of the present invention.

EXAMPLES

Examples 1 through 12 were prepared to illustrate the ability to produce alcohol-based formulations which can be dispensed as foams using different surfactants and a solution of water and 50% ethanol. Examples 13 through 18 show increasing concentrations of ethanol and fluorosurfactant to produce foam. Examples 19 through 30 illustrate the ability to produce foam using different surfactants and a solution of 70% v/v Isopropanol. All parts and percentages are expressed by weight unless otherwise indicated.

| Amount Ingredients | Ex. 1 | Ex. 2 | Ex. 3 | Ex. 4 | Ex. 5 | Ex. 6 |
|---|---|---|---|---|---|---|
| S.D. Alcohol 3-A | 50.00 | 50.00 | 50.00 | 50.00 | 50.00 | 50.00 |
| Fluorosurfactant | 0.50 | — | — | — | — | — |
| Cocamidopropyl betaine (1) | — | 8.00 | — | — | — | — |
| Alkylglucoside (2) | — | — | 8.00 | — | — | — |
| Alkylglucoside (3) | — | — | — | 8.00 | — | — |
| Glycomul L | — | — | — | — | 8.00 | — |
| Sorbitan Sesquioleate | — | — | — | — | — | 8.00 |
| Deionized Water | 49.50 | 42.00 | 42.00 | 42.00 | 42.00 | 42.00 |
| Total % | 100.00 | 100.00 | 100.00 | 100.00 | 100.00 | 100.00 |

| Amount Ingredients | Ex. 7 | Ex. 8 | Ex. 9 | Ex. 10 | Ex. 11 | Ex. 12 |
|---|---|---|---|---|---|---|
| S.D. Alcohol 3-A | 50.00 | 50.00 | 50.00 | 50.00 | 50.00 | 50.00 |
| Polysorbate 20 | 8.00 | — | — | — | — | — |
| Polyoxyethylene Sorbitan Monooleate | — | 8.00 | — | — | — | — |
| Sorbitan Monooleate | — | — | 8.00 | — | — | — |
| Cocamidopropyl betaine & sodium caproyl lactate | — | — | — | 8.00 | — | — |
| Cocamidopropyl hydroxysultaine | — | — | — | — | 8.00 | — |
| Sodium Cocoamphoacetate | — | — | — | — | — | 8.00 |
| Deionized Water | 42.00 | 42.00 | 42.00 | 42.00 | 42.00 | 42.00 |
| Total % | 100.00 | 100.00 | 100.00 | 100.00 | 100.00 | 100.00 |

| Amount Ingredients | Ex. 13 | Ex. 14 | Ex. 15 | Ex. 16 | Ex. 17 | Ex. 18 |
|---|---|---|---|---|---|---|
| S.D. Alcohol 3-A | 50.00 | 60.00 | 65.00 | 70.00 | 80.00 | 92.50 |
| Fluorosurfactant | 0.10 | 0.75 | 0.80 | 1.50 | 2.00 | 7.5 |
| Deionized Water | 49.90 | 39.25 | 34.20 | 28.50 | 18.00 | — |
| Total % | 100.00 | 100.00 | 100.00 | 100.00 | 100.00 | 100.00 |

| Amount Ingredients | Ex. 19 | Ex. 20 | Ex. 21 | Ex. 22 | Ex. 23 | Ex. 24 |
|---|---|---|---|---|---|---|
| 70% v/v Isopropanol | 99.90 | 92.00 | 92.00 | 92.00 | 92.00 | 92.00 |
| Fluorosurfactant | 0.10 | — | — | — | — | — |
| Cocamidopropyl betaine (1) | — | 8.00 | — | — | — | — |
| Alkylglucoside (2) | — | — | 8.00 | — | — | — |
| Alkylglucoside (3) | — | — | — | 8.00 | — | — |
| Glycomul L | — | — | — | — | 8.00 | — |
| Sorbitan Sesquioleate | — | — | — | — | — | 8.00 |
| Total % | 100.00 | 100.00 | 100.00 | 100.00 | 100.00 | 100.00 |

| Amount Ingredients | Ex. 25 | Ex. 26 | Ex. 27 | Ex. 28 | Ex. 29 | Ex. 30 |
|---|---|---|---|---|---|---|
| 70% v/v Isopropanol | 92.00 | 92.00 | 92.00 | 92.00 | 92.00 | 92.00 |
| Polysorbate 20 | 8.00 | — | — | — | — | — |
| Polyoxyethylene Sorbitan Monooleate | — | 8.00 | — | — | — | — |
| Sorbitan Monooleate | — | — | 8.00 | — | — | — |
| Cocamidopropylbetaine & sodium caproyl lactate | — | — | — | 8.00 | — | — |
| Cocamidopropyl hydroxysultaine | — | — | — | — | 8.00 | — |
| Sodium Cocoamphoacetate | — | — | — | — | — | 8.00 |
| Total % | 100.00 | 100.00 | 100.00 | 100.00 | 100.00 | 100.00 |

(1) Amphoteric,
(2) Nonionic,
(3) Anionic

The solutions prepared, were evaluated as to whether foam was produced or not and if so, then the foam produced was described as follows:

| Example | Foam Produced | Foam Evaluation/Description/Characteristics |
|---|---|---|
| Ex. 1 | Yes | Very good stable stiff puff creamy and soft lasts minutes |
| Ex. 2 | No | Just Very Wet Bubbles produced lasting <10 seconds |
| Ex. 3 | No | — |
| Ex. 4 | No | — |
| Ex. 5 | No | — |
| Ex. 6 | No | Just Very Wet Bubbles produced lasting <7 seconds |
| Ex. 7 | No | Just Very Wet Bubbles produced lasting <10 seconds |
| Ex. 8 | No | — |
| Ex. 9 | No | Just Very Wet Bubbles produced lasting <10 seconds |
| Ex. 10 | No | — |
| Ex. 11 | No | — |
| Ex. 12 | No | — |
| Ex. 13 | Yes | Very good stable stiff puff creamy and soft lasts minutes |
| Ex. 14 | Yes | Very good creamy and soft lasts more than a minute |
| Ex. 15 | Yes | Very good creamy and soft lasts more than a minute |
| Ex. 16 | Yes | Very good creamy and soft lasts more than a minute |
| Ex. 17 | Yes | Quick fast breaking foam lasts more than a 15 secs |
| Ex. 18 | Yes | Quick fast breaking foam lasts more than a 10 secs |
| Ex. 19 | Yes | Quick fast breaking foam lasts more than a 20 secs |
| Ex. 20 | No | — |
| Ex. 21 | No | — |
| Ex. 22 | No | — |
| Ex. 23 | No | — |
| Ex. 24 | No | — |

-continued

| Example | Foam Produced | Foam Evaluation/Description/Characteristics |
|---------|---------------|---------------------------------------------|
| Ex. 25  | No            | —                                           |
| Ex. 26  | No            | —                                           |
| Ex. 27  | No            | —                                           |
| Ex. 28  | No            | —                                           |
| Ex. 29  | No            | —                                           |
| Ex. 30  | No            | —                                           |

Comparatively, it was also found that for instance, Cocamidopropyl betaine (CAPB) alone even at 40% ethanol and at 3% CAPB, was unable to produce as good results as those with 60% v/v ethanol, and fluorosurfactants using much less percentage (less than 1.0%). Cocamidopropyl betaine does not give any acceptable foam above that percentage of alcohol and the lower than 60% v/v alcohol content makes it inadequate for a sanitizing solution. Also the solution left an unacceptable feeling on the skin after the alcohol evaporated (i.e. a soapy sticky feeling) indicating high levels of surfactant.

Very interestingly fluorosurfactants seemed to be a likely way to achieve a foaming composition that contains more than 40% v/v alcohol. The fact that foam could be achieved even when no added water or ingredients are used other than 95% v/v alcohol and the fluorosurfactant as shown in example 18 makes the present invention suitable for many different applications.

Below are some specific examples for compositions following the above formulation to produce alcohol hand sanitizing solutions; more than one being a foamable composition with alcohol being the only disinfectant ingredient, while other foamable compositions use an added antimicrobial such as Chlorhexidine Digluconate or Didecyl Dimethyl Diammonium Chloride and the third group being alcohol gel-like hand sanitizing solutions.

Example 31

Alcohol hand sanitizing foamable disinfecting composition 0.01-1.0%*amphoteric, anionic or non-ionic fluorosurfactant (primary surfactant)

0.01-1.0% cocoamidopropylbetaine (secondary surfactant)

0.05-1.0% cetyl betaine (foam stabilizing agent)

0.10-1.5% emulsifier fatty alcohol ROH 16-22 carbons or combination that works well in a final formulation containing 60-70% v/v ethanol Q.S. water Preferably Polytetrafluoroethylene Acetoxypropyl Betaine $CF_3CF_2(CF_2CF_2)_nCH_2CH_2(OAc)CH_2N^+(CH_3)_2CH_2COO^-$, where n=2-4 or an ethoxylated nonionic fluorosurfactant of the following structure: $RfCH_2CH_2O(CH_2CH_2O)_xH$ where $Rf=F(CF_2CF_2)y$, x=0 to about 15 and y=1 to about 7; or an anionic phosphate fluorosurfactant of the following structure: $(RfCH_2CH_2O)_xP(O)(ONH_4)_y$ where $Rf=F(CF_2CF_2)z$, x=1 or 2, y=2 or 1, x+y=3, and z=1 to about 7, or mixtures thereof.

Example 32

Alcohol Hand Sanitizing Foamable Disinfecting Composition Concentrate 0.01-1.0%*amphoteric, anionic or non-ionic fluorosurfactant (primary surfactant)

0.01-12.0% 1,3 Butyleneglycol, 2-Butoxyethanol, n-propanol (foam stabilizing agents)

0.05-5.0% cocoglucoside, glycerin, glyceryl oleate (moisturizers, emollients and the like)

60-70% v/v ethanol, n-propanol, isopropanol or a combination thereof

Q.S. water

Preferably an anionic phosphate fluorosurfactant of the following structure: $(RfCH_2CH_2O)_xP(O)(ONH_4)_y$ where $Rf=F(CF_2CF_2)z$, x=1 or 2, y=2 or 1, x+y=3, and z=1 to about 7 or an ethoxylated nonionic fluorosurfactant of the following structure: $RfCH_2CH_2O(CH_2CH_2O)_xH$ where $Rf=F(CF_2CF_2)y$, x=0 to about 15 and y=1 to about 7; or Polytetrafluoroethylene Acetoxypropyl Betaine $CF_3CF_2(CF_2CF_2)_nCH_2CH_2(OAc)CH_2N^+(CH_3)_2CH_2COO^-$, where n=2-4, or mixtures thereof Example 33

Alcohol Hand Sanitizing Foamable Disinfecting Composition a) ethanol present in an amount between about 60% to 70% percent v/v of the total composition;

b) a physiologically acceptable anionic phosphate fluorosurfactant in an amount from about 0.01% to about 2.0% weight percent of the total composition;

c) at least 1% n-propanol d) foam stabilizing agents that at least include 1,3-Butyleneglycol % 2, Butoxyethanol in 0.001-3% ea.

e) a lipid layer enhancer such as a mixture of alkylglucoside and glyceryl oleate f) water in an amount to balance the total composition to 100% weight percent.

Example 34

Chlorhexidine Gluconate (CHG) & Alcohol Hand Sanitizing Foamable Disinfecting Composition Formulations 31 or 32 added with 0.50-4.0% Chlorhexidine Gluconate (CHG)

Example 35

Formulations 31 or 32 added with 0.01-5.0% Didecyl Dimethyl Diammonium Chloride

Example 36

Alcohol Hand Sanitizing Gel-Like Disinfecting Composition with a Viscosity Less than 4,000 Cps 0.0-1.0%*amphoteric, anionic or non-ionic fluorosurfactant (primary surfactant)

0.10-2.0% an emulsifier moisturizer and/or emollient preferably a non-ionic surfactant and/or a combination of cetearyl alcohol and ceteareth 20 or a combination thereof to give a composition with a viscosity of less than 4,000 cps;

0.50-4.0% a combination of nonionic surfactants specifically from the group of the polyethoxylated fatty alcohols 60-70% v/v ethanol Q.S. water Preferably Polytetrafluoroethylene Acetoxypropyl Betaine $CF_3CF_2(CF_2CF_2)_nCH_2CH_2(OAc)CH_2N^+(CH_3)_2 CH_2COO^-$, where n=2-4 or an ethoxylated nonionic fluorosurfactant of the following structure: $RfCH_2CH_2O(CH_2CH_2O)_xH$ where $Rf=F(CF_2CF_2)y$, x=0 to about 15 and y=1 to about 7; or an anionic phosphate fluorosurfactant of the following structure: $(RfCH_2CH_2O)_xP(O)(ONH_4)_y$, where $Rf=F(CF_2CF_2)z$, x=1 or 2, y=2 or 1, x+y=3, and z=1 to about 7, or mixtures thereof.

The process to prepare the compositions of the present invention described herein is straightforward since most of the ingredients are liquid. When wax type ingredients are to be used, they can be incorporated by warming up to 40-45° C. preferably to the alcohol portion while mixing and then allowing it to cool down or they could be added in "cold", at room temperature to the alcohol before any other ingredient and mixed until completely incorporated before adding the rest of the ingredients according to the composition. Whether all ingredients are liquid or not, warming from 30 to 80 degrees Celsius, (depending on the particular composition) increases the long term stability of the compositions. Active ingredients could be pre-dissolved into the water first. A process that anyone knowledgeable enough of the art would have no problem implementing. If a specific formulation cannot be adjusted for the foamable composition in the percentages of the ingredients, then there is still the option of modifying the characteristics of the foaming pump, such as changing pressures, screen sizes, etc.

The compositions described within the present invention improve over prior similar products commercially available in the high concentrations of alcohol, as well as in the fact of being able to foam even with no propellants or pressurized containers (using propellants would improve considerably the quality of the foam) and being able to produce alcohol gel-like compositions that do not leave a sticky after-feel that builds up and do not clog the dispensers after single or multiple applications.

Depending on the alcohol concentration and the application of the particular composition the foam produced can widely vary, being at the high end of a relatively fast breaking variety stable enough to be thoroughly spread onto the skin without waste in a unique way and the gel-like composition viscosity varies with the alcohol concentration. The gel-like composition obtained is a unique approach that does not follow the traditional ways of making alcohol gels. In summary it could be said that the stated invention has exceeded expectations.

Due to the nature of the base composition with respect to the alcohol concentration and the quality of the ingredients, one of the logical first applications for the present invention would be as an alcohol hand disinfectant composition either for a foamable product or an alcohol gel-like product, examples of which are described above. Nevertheless, the present invention lends itself to the preparation of a wide variety of products, and it is to be understood that other embodiments may be utilized and that changes may be made without departing from the scope of the invention.

Consequently, it is intended that the claims be interpreted to cover such modifications and equivalents. To note a few, the following may be mentioned: medicated foams and gels, sunscreen foams and gels, hand cream foams, brush-less shaving cream foams, shower or bath oil foams, dry hair shampoo foams, make-up remover foams, analgesic foam rubs and gels, hair grooming foams and antiperspirants hair cleaning foam, antiperspirant foam, hair conditioner foams.

As used herein, the terms "comprises", "comprising", "includes" and "including" are to be construed as being inclusive and open ended, and not exclusive. Specifically, when used in this specification including claims, the terms "comprises", "comprising", "includes" and "including" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

References Cited
U.S. PATENT DOCUMENTS

| | | | |
|---|---|---|---|
| 2,054,989 | September 1936 | Moore | 167/58 |
| 3,131,153 | April 1964 | Klausner | 252/305 |
| 3,962,150 | June 1976 | Leonard et al. | 252/542 |
| 4,440,653 | April 1984 | James et al. | 252/8.55 |
| 5,167,950 | December 1992 | Lins | 424/47 |
| 4,956,170 | September 1990 | Lee | 514/772.1 |
| 5,629,006 | May 1997 | Minh et al. | 424/405 |
| 5,906,808 | May 1999 | Osborne, et al. | 424/43 |
| 5,928,993 | July 1999 | Ingegärd | 504/116 |
| 5,951,993 | September 1999 | Scholz et al. | 424/405 |
| 6,090,395 | July 2000 | Asmus et al. | 424/401 |
| 6,610,315 | August 2003 | Scholz et al. | 424/415 |
| 6,623,744 | September 2003 | Asmus et al. | 424/401 |
| 6,562,360 | May 2003 | Scholz et al. | 424/405 |

OTHER PUBLICATIONS

Myers, Drew: "Surfactant Science and Technology", second edition, Drew Myers, VCH Publishers, New York, 1992

Reduce Tension Dupont Zonyl® Fluorosurfactants Field Manual published by Dupont Co on May 2001

What is claimed is:

1. A method of forming a skin disinfecting foam containing alcohol, comprising the steps of:
   activating a dispenser pump of an unpressurized dispenser to combine an alcohol-fluorosurfactant mixture with air to form and dispense a skin disinfecting foam containing alcohol, wherein the alcohol-fluorosurfactant mixture comprises an alcohol $C_{1-4}$, or mixtures thereof, present in an amount greater than or equal to about 60% v/v of the total composition, a physiologically acceptable effective anionic phosphate fluorosurfactant for foaming present in an amount of at least 0.001% by weight of the total composition, and water present in an amount to balance the total composition to 100% by weight.

2. The method of claim 1 wherein the effective physiologically acceptable fluorosurfactant is for wetting.

3. The method according to claim 1 wherein the effective physiologically acceptable fluorosurfactant is present in an amount from about 0.001% to about 10.0% by weight of the total composition.

4. The method according to claim 1 wherein the alcohol $C_{1-4}$ is an aliphatic alcohol selected from the group consisting of methanol, ethanol, isopropanol, n-propanol, butanol and combinations thereof.

5. The method according to claim 1 wherein the alcohol is present in a range from about 60% to about 90% v/v.

6. The method according to claim 1 further including at least one additional surfactant for adjusting properties of the foam produced from the composition.

7. The method according to claim 6 wherein the additional surfactant is selected from the group consisting of a poly(ethoxylated and/or propoxylated)alcohol, a poly(ethoxylated and/or propoxylated)ester, a derivative of a poly(ethoxylated and/or propoxylated)alcohol, a derivative of a poly(ethoxylated and/or propoxylated)ester, an alkyl alcohol, an alkenyl alcohol, an ester of a polyhydric alcohol, an ether of a polyhydric alcohol, an ester of a polyalkoxylated derivative of a polyhydric alcohol, an ether of a polyalkoxylated derivative of a polyhydric alcohol, a sorbitan fatty acid ester, a polyalkoxylated derivative of a sorbitan fatty acid ester, an alkylglucoside, a betaine, a sulfobetaine, an imidazoline derivative, an aminoacid derivative, a lecithin, a phosphatide, an amine oxide, a sulfoxide and mixtures thereof, present in an amount between about 0.10% to about 5% by weight.

8. The method according to claim 1, wherein the composition does not include a propellant.

9. A method for personal disinfecting comprising:
applying to a person's skin a skin-disinfecting alcohol foam composition which comprises
a) air mixed under low pressure conditions with
b) a liquid comprising
i) an alcohol $C_{1-4}$, or mixtures thereof, present in an amount greater than or equal to about 60% v/v of the total composition;
ii) water present in an amount to balance the total composition to 100% by weight; and
iii) a physiologically acceptable effective anionic phosphate fluorosurfactant for foaming present in an amount of at least 0.001% by weight of the total composition.

10. The method according to claim 9 wherein the effective physiologically acceptable fluorosurfactant is for wetting.

11. The method according to claim 9 wherein the effective physiologically acceptable fluorosurfactant is present in an amount from about 0.001% to about 10.0% by weight of the total composition.

12. The method according to claim 9 wherein the alcohol $C_{1-4}$ is an aliphatic alcohol selected from the group consisting of methanol, ethanol, isopropanol, n-propanol, butanol and combinations thereof.

13. The method according to claim 9 wherein the alcohol is present in a range greater than about 60% v/v to about 90% v/v.

14. The method according to claim 9 wherein the alcohol is ethanol present in an amount of at least 60% v/v.

15. The method according to claim 9 wherein the alcohol is a mixture of n-propanol and ethanol present in a combined amount of at least 60% v/v.

16. The method according to claim 9 wherein the alcohol is a mixture of isopropanol and ethanol present in a combined amount of at least 60% v/v.

17. The method according to claim 9 wherein the alcohol is isopropanol present in an amount of at least 70% v/v.

18. The method according to claim 9 wherein the alcohol is n-propanol present in an amount of at least 60% v/v.

19. The method according to claim 9 wherein the alcohol foam composition further includes at least one additional surfactant for adjusting properties of the composition and/or the resulting foam produced from the composition.

20. The method according to claim 19 wherein the additional surfactant is selected from the group consisting of a poly(ethoxylated and/or propoxylated)alcohol, a poly(ethoxylated and/or propoxylated)ester, a derivative of a poly(ethoxylated and/or propoxylated)alcohol, a derivative of a poly(ethoxylated and/or propoxylated)ester, an alkyl alcohol, an alkenyl alcohol, an ester of a polyhydric alcohol, an ether of a polyhydric alcohol, an ester of a polyalkoxylated derivative of a polyhydric alcohol, an ether of a polyalkoxylated derivative of a polyhydric alcohol, a sorbitan fatty acid ester, a polyalkoxylated derivative of a sorbitan fatty acid ester, an alkyglucoside, a betaine, a sulfobetaine, an imidazoline derivative, an aminoacid derivative, a lecithin, a phosphatide, an amine oxide, a sulfoxide and mixtures thereof, present in an amount between about 0.10% to about 5% by weight.

21. The method according to claim 20 wherein the betaine is cocamidopropyl betaine.

22. The method according to claim 20 wherein the alkylglucoside is cocoglucoside.

23. The method according to claim 20 wherein the polyethoxylated fatty alcohol is polyethoxylated stearyl alcohol (21 moles ethylene oxide).

24. The method according to claim 20 wherein the polyethoxylated fatty alcohol is polyethoxylated stearyl alcohol (2 moles ethylene oxide).

25. The method according to claim 20 wherein the polyethoxylated fatty alcohol is a combination of polyethoxylated stearyl alcohol (21 moles ethylene oxide) and polyethoxylated stearyl alcohol (2 moles ethylene oxide).

26. The method according to claim 9 wherein the alcohol foam composition includes a foam stabilizing agent present in an amount up to 5% by weight.

27. The method according to claim 26 wherein the foam stabilizing agent is selected from the group consisting of lactic acid esters of monoglycerides, cationic emulsifiers, triquaternized stearic phospholipid complex, hydroxystearamide propyltriamine salts, lactic acid monoglycerides, food emulsifiers selected from the group consisting of glyceryl monostearate, propylene glycol monostearate, sodium stearoyl lactylate, cetyl betaine, glycolether, n-propanol, butyleneglycol, silicone wax, an encapsulated oil, Microcapsule Mineral Oil®, and combinations thereof.

28. The method according to claim 26 wherein the foam stabilizing agent is selected from the group consisting of glycolether, n-propanol, butyleneglycol, and combinations thereof.

29. The method according to claim 9 wherein the effective physiologically acceptable fluorosurfactant is present in an amount from about 0.1% to about 10.0% by weight of the total composition.

30. A method for producing, and applying to a person's skin, a skin-disinfecting alcohol foam composition, comprising:
activating a dispenser pump of an unpressurized dispenser to combine an alcohol-fluorosurfactant mixture with air to form and dispense a skin-disinfecting alcohol foam, the alcohol-fluorosurfactant mixture comprising an alcohol $C_{1-4}$, or mixtures thereof, present in an amount greater than or equal to about 60% v/v of the total composition, a physiologically acceptable anionic phosphate fluorinated surface active agent present in an amount of at least 0.001% by weight of the total composition, and water present in an amount to balance the total composition to 100% by weight; and
applying the skin-disinfecting alcohol foam to the person's skin.

31. The method according to claim 30 wherein the effective physiologically acceptable fluorinated surface active agent is a fluorosurfactant present in an amount from about 0.1% to about 10.0% by weight of the total composition.

32. An unpressurized dispenser having a dispenser pump for mixing a composition with air and dispensing foam therefrom, said composition comprising:
- an alcohol $C_{1-4}$, or mixtures thereof, present in an amount greater than or equal to about 60% v/v of the total composition,
- a physiologically acceptable effective anionic phosphate fluorosurfactant for foaming present in an amount of at least 0.001% by weight of the total composition, and
- water present in an amount to balance the total composition to 100% by weight.

33. The dispenser of claim 32 wherein the effective physiologically acceptable fluorosurfactant is present in an amount from about 0.1% to about 10.0% by weight of the total composition.

34. The method of claim 1 wherein the alcohol-fluorosurfactant mixture further comprises glycerol.

35. The method of claim 9 wherein the liquid further comprises glycerol.

36. The method of claim 30 wherein the alcohol-fluorosurfactant mixture further comprises glycerol.

37. The unpressurized dispenser of claim 32 wherein the composition further comprises glycerol.

* * * * *